United States Patent [19]
Golub et al.

[11] Patent Number: 6,143,506
[45] Date of Patent: Nov. 7, 2000

[54] DIAGNOSTIC METHOD FOR DETECTION OF PERIODONTITIS OR PERI-IMPLANTITIS

[75] Inventors: Lorne M. Golub, Smithtown, N.Y.; Timo Sorsa, Helsinki, Finland; Olli Teronen, Helsinki, Finland; Sari Hannele Tikanoja, Helsinki, Finland

[73] Assignee: The Research Foundation of State of NY, Albany, N.Y.

[21] Appl. No.: 09/133,887

[22] Filed: Aug. 13, 1998

[51] Int. Cl.[7] .................................................... G01N 33/53

[52] U.S. Cl. ............................ 435/7.1; 435/7.4; 435/7.9; 435/7.92; 435/7.94; 435/7.95; 435/23; 436/518; 436/531; 436/516

[58] Field of Search ............................. 435/7.1, 7.4, 7.9, 435/7.92, 7.94, 7.95, 23; 436/518, 531, 516

[56] References Cited

U.S. PATENT DOCUMENTS 5,736,341  4/1998  Sorsa et al. .............................. 435/7.1

OTHER PUBLICATIONS

Golub et al. "A matrix metalloproteinase inhibitor reduces bone–type collagen degradation fragments and specific collagenases in gingival crevicular fluid during adult periodontitis", *Inflammation Research,* vol. 46, No. 8(Aug. 1997) pp. 310–319. RM1.A3.

Harlow et al. *Antibodies: A Laboratory Manual.* N.Y., Cold Spring Harbor, 1988. pp. 8, 141, 142, 555 and 556. QR186.7.A53.

Uitto, V.J., Airola, K., Vaalamo, M., Johansson, N., Putnins, E.E., Firth, J.D., Salonen, J., Lopez–Otin, C., Saarialho–Kere, U., Kahari, V–M, "Matrix Metalloproteinase–13 is a Major Collagenase in Inflamed Human Gingiva", *Journal of Dental Research,* 77:Abstract No. 2904 (1998).

Giannobile, W.V., Lee, H.M., Ryan M.E., Golub L.M., "Low Dose Doxcycline (LDD) Reduces Bone–type Collagen Degradation Fragments in Gingival Fluid", *Journal of Dental Research,* 76:Abstract No. 1306 (1997).

*Primary Examiner*—Jeffrey Stucker
*Attorney, Agent, or Firm*—Hoffmann & Baron, LLP

[57] ABSTRACT

The invention relates to methods and test kits for diagnosis of periodontal disease activity in mammals, especially in human. The methods of the invention provide for rapid chair-side diagnosis of periodontitis, peri-implantitis and HIV (+)-infection/AIDS-disease related periodontal diseases. Especially, the methods of the invention provide for rapid chair-side diagnosis of the loss of bone density associated with periodontal diseases.

8 Claims, 7 Drawing Sheets

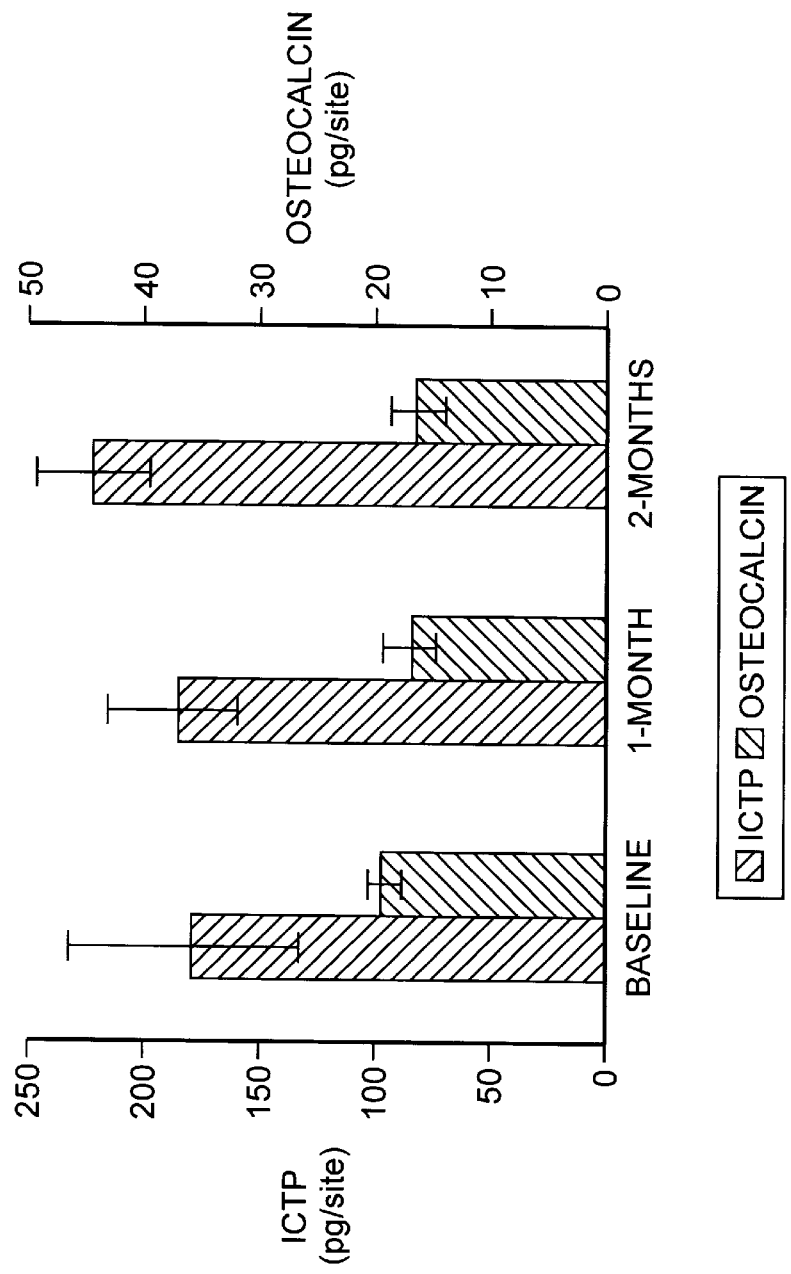
FIG. 1 GROUP I (Controls)

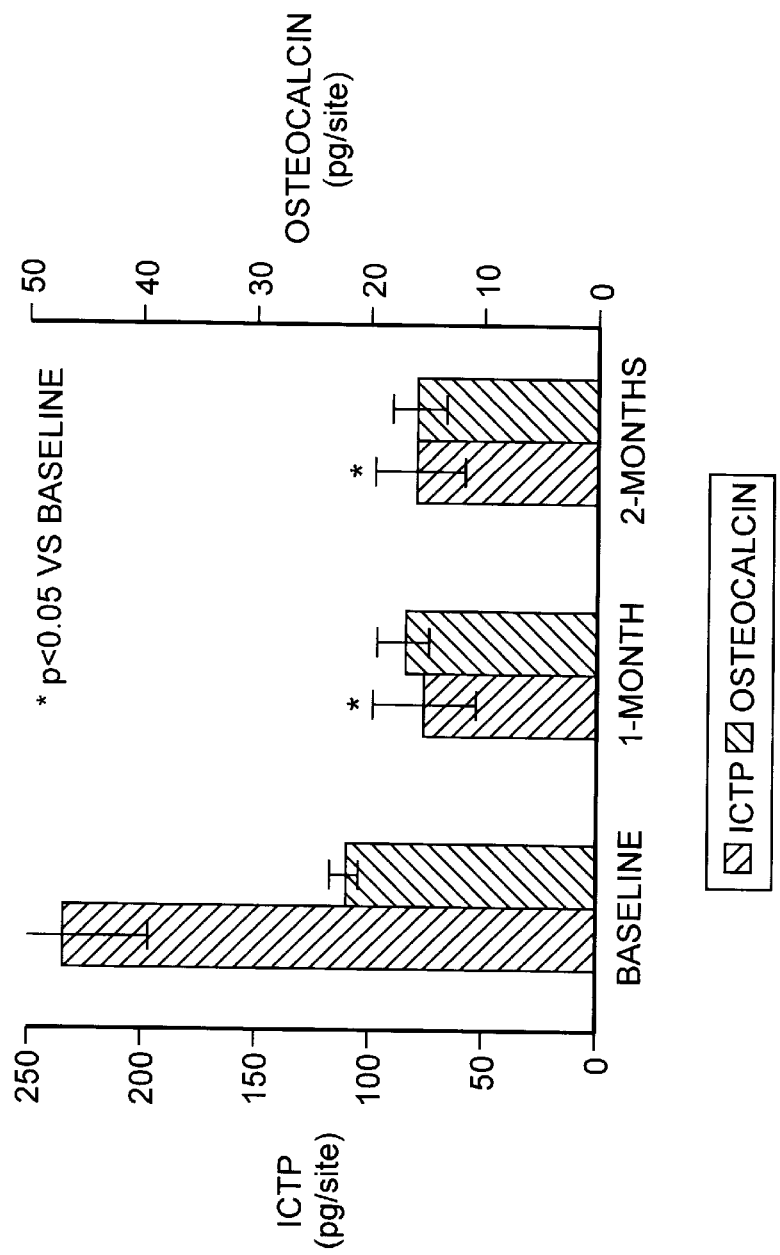
FIG. 2 GROUP II (LDD)

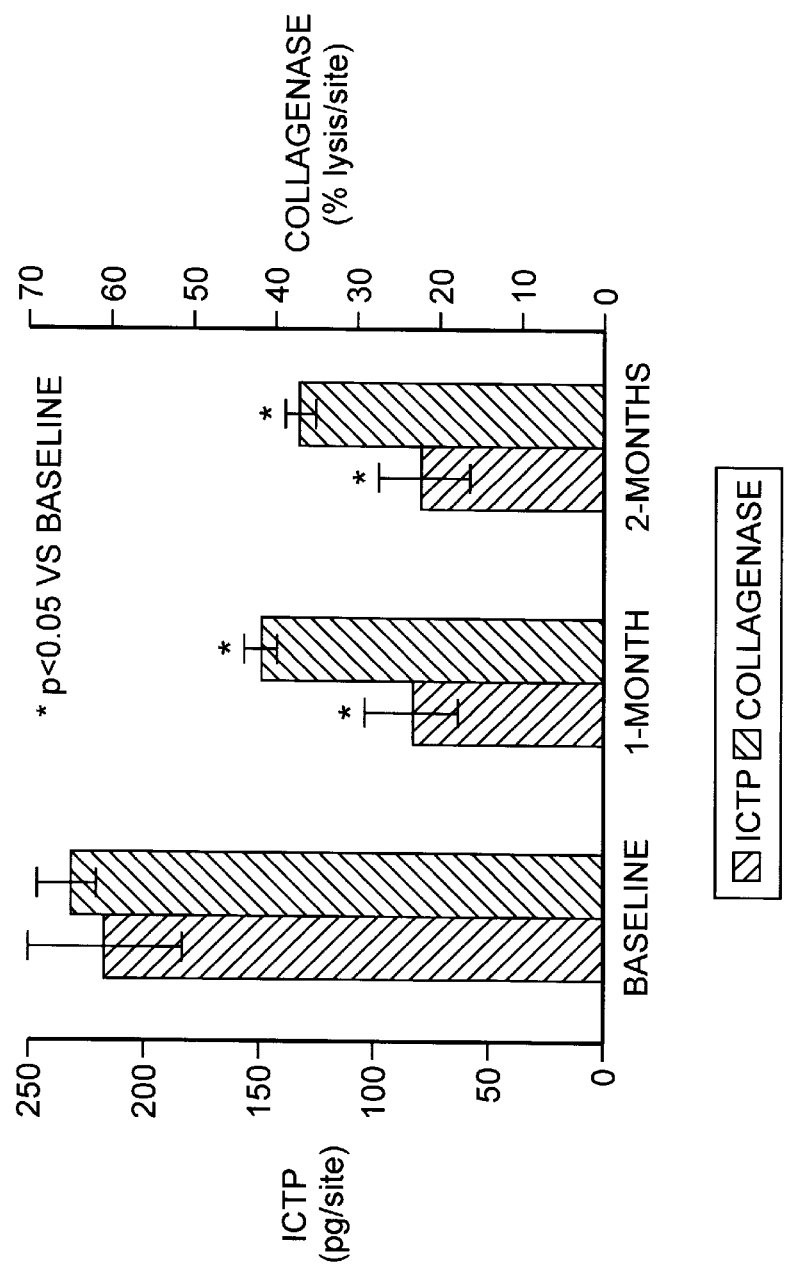
FIG. 3  GROUP III (LDD)

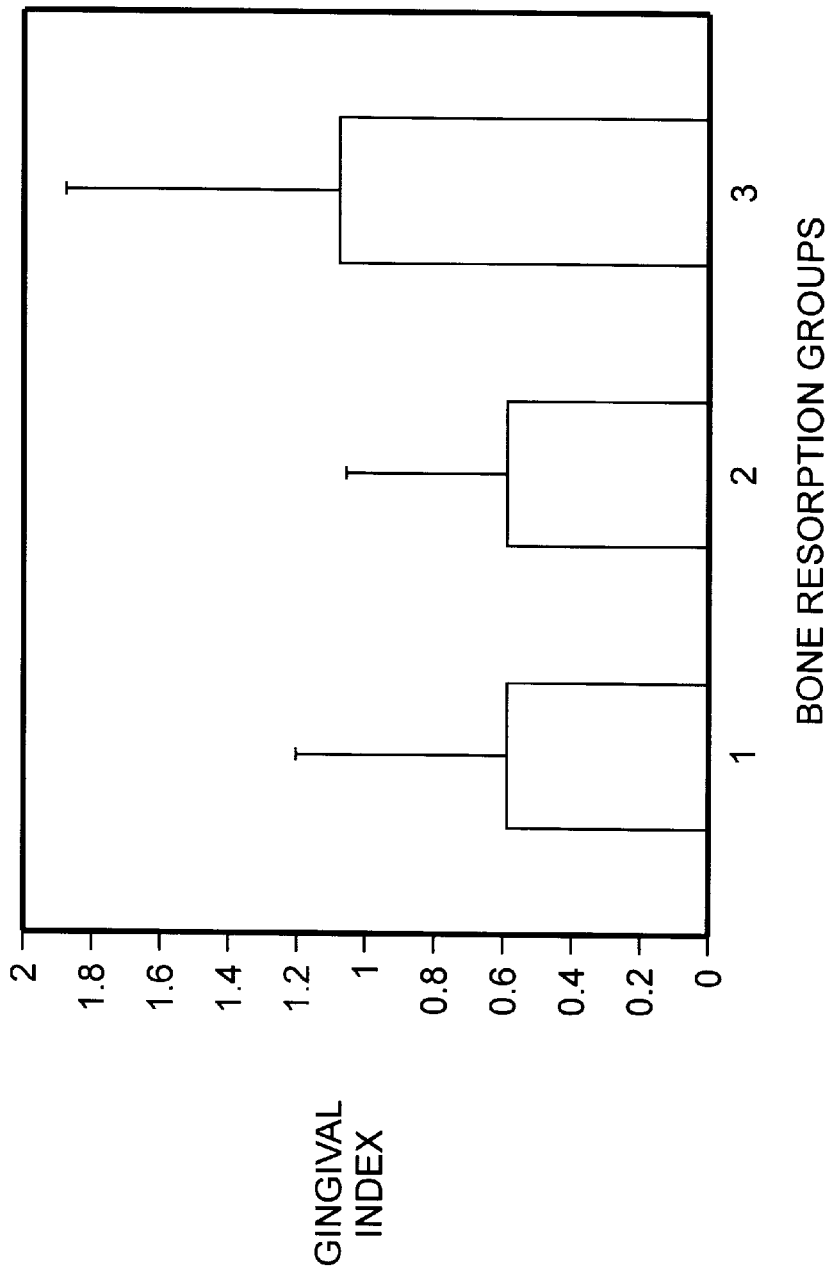
FIG. 5  GINGIVAL INDEX / BONE RESORPTION

DIAGNOSTIC METHOD FOR DETECTION OF PERIODONTITIS OR PERI-IMPLANTITIS

This invention was made with Government support under Grant Nos. R37DE-03987, K16DE-00275, and K11DE-00363 awarded by the National Institutes of Health through the National Institute of Dental Research. The Government has certain rights in the invention.

BACKGROUND OF THE INVENTION

The invention relates to methods and test kits for diagnosis of periodontal disease activity in mammals, especially in human. The methods of the invention provide for rapid chair-side diagnosis of periodontitis, peri-implantitis and HIV (+)-infection/AIDS-disease related periodontal diseases. Especially, the methods of the invention provide for rapid chair-side diagnosis of the loss of bone density associated with periodontal diseases.

Periodontal diseases are a major problem in the human dentition. In fact, more teeth are lost from periodontal disease than from dental caries. Thus, there is a great need for reliable diagnostic tests for periodontal disease.

Periodontal disease comprises a group of inflammatory disorders originating from infections affecting the gingiva (gum), periodontal ligament (a periodontal structural element/tissue linking tooth to alveolar bone) and the alveolar (jaw) bone structures supporting the teeth. The primary cause of periodontal diseases is bacterial plaque attached to the teeth. This causes inflammation of the gum which may result in destruction of the actual tooth-supporting structure and bone. In periodontal disease, there is usually a large accumulation of bacteria in plaque, both above (supragingival) and below (subgingival) the gum line. The plaque can calcify and form calculus deposits. The calculus deposit and associated plaque can create a "pocket" between the teeth and the gingiva which is an irreversible characteristic of periodontal disease.

Gingivitis (gum inflammation) is distinguished from periodontitis in that in gingivitis, gingiva are inflamed but no deep (>4 mm) periodontal pockets are detectable; thus, no irreversible destruction of tooth supporting structures is associated with gingivitis. Periodontitis is characterized by inflamed gingiva and destruction of tooth supporting structures; however, periodontitis can be missed in clinically-healthy-looking gingiva.

Several methods for detecting periodontal disease have been developed (Armitage, G. C., C.D.A. Journal 36, 35–41, 1993). However, none of the presently available detection methods is sufficiently accurate and specific to provide a reliable tool for diagnosing and assessing the hard tissue destruction associated with periodontal diseases, including peri-implantitis and HIV (+)-infections/AIDS-related periodontal diseases.

Especially, several attempts to develop methods for assessing progressing periodontitis, as discussed below, have been tested but none of them have been found to be satisfactory enough to create a rapid and reliable chair-side test for the hard tissue destruction (bone resorption) associated with periodontal disease.

Visual examination

When gingiva (gums) are affected by periodontal disease, color change (from pink to red), texture alterations (redness and swelling), and an increased tendency to bleed (in that particular gingival and sulcular/sulcus area) can be detected. Advanced stage periodontal disease is frequently associated with increased tooth mobility and drifting of the teeth.

However, some forms of periodontal disease, such as localized juvenile periodontitis (LJP), can have a treacherous nature and a misleading clinical course. Thus, active local periodontitis is not always detectable by visual examinations. Consequently, biochemical adjunctive means to help the clinical diagnosis of juvenile periodontitis would be desirable and helpful for prompt and adequate early diagnosis, as well as identification and screening, especially in case of young patients.

Clinical assessment of periodontal status and probing of periodontal lesions.

Currently, periodontal disease is diagnosed by clinical observation of indicators such as presence and depths of periodontal pockets, loss of attachment of the teeth to the bone, and papillary bleeding of the gums. Clinical observations, however, are not always reliable indicators. For example, even deep periodontitis pockets containing putative periodontal pathogens are not necessarily indicative of disease activity or periodontal tissue destruction.

Periodontal attachment levels can be assessed by means of a graduated periodontal probe and expressed as the distance from the cement enamel junction to the bottom of the gingival pocket. The longer distance for each tooth surface is recorded and may be included in the periodontium chart. Pocket depth values <4 mm are excluded from the chart as falling within normal variations. Thus, pockets >4 mm are considered as periodontitis pockets or periodontitis lesions.

As a measurement technique, periodontal probing has several sources of error. The extent of probe penetration varies with insertion force, inflammatory status of the periodontal tissues, and diameter of probe tip. Measurement errors resulting from thickness of the probe, contour of the tooth surface and improper angulation of the probe can be reduced or avoided by the selection of a proper instrument and careful management of the examination procedure. More difficult to avoid, however, are errors resulting from variations in probing force and inflammation of the periodontal tissues. The measurement errors limit the accuracy and reproducibility.

Automated periodontal probes have also been developed. The primary advantage is controlled insertion force, reproducibility, and direct data entry. The main disadvantages include reduced tactile sense of operator and patient discomfort.

Noteworthy, gingivitis or gum inflammation is distinguished from periodontitis by the facts that in gingivitis, unlike periodontitis, gingiva is inflamed but no deep (>4 mm) periodontal pockets can be detected; thus, no irreversible degradation (destruction) of tooth supporting structures either detected by probing and/or radiographically is associated with gingivitis. Periodontitis is characterized by inflamed gingiva and destruction of tooth supporting structures; however, periodontitis can well exist under the "clinically-healthy-looking" gingiva.

In conclusion, it is clear that clinical observations are not always reliable indicators. A further problem is the difficulty to assess an progressing periodontal disease because in some cases deep periodontitis pockets—even harboring putative periodontopathogens—are not necessarily active in regard to the inflammatory periodontal tissue destruction.

Radiographic evaluation

Sequential radiographic images have also been used to evaluate periodontal disease activity. The loss of bone density at the alveolar crest is frequently a sign of progression of periodontitis.

The height of the alveolar (jaw) bone and the outline of the bone crest can be examined in the radiographs. The radiographs provide information of the height and configuration of the interproximal alveolar bone. However, the radiographic assessment of the periodontal disease activity has drawbacks. Even with an excellent set of films and an experienced examiner, the unaided eye can only detect changes in bone after 30–50 percent of the bone mineral has been lost. Cover structures (bone, tissue, teeth) often make it difficult to properly identify the outlines of buccal and lingual alveolar crests. The analysis of radiographs is to be combined with a detailed evaluation of the pocket depths and the attachment level data to obtain a correct and exact diagnosis. Upon recalls (examinations of treated periodontitis patients) radiographic examination is required.

In summary, periodontal probes and radiographs measure two separate components in the progression of periodontitis. One provides an estimate of the attachment loss of soft tissue from the tooth surface and the other measures loss of bone density.

Biological Tests

In addition to periodontal probing, biological (microbial and biochemical) tests have been designed to provide information associated with progressing periodontal lesions. These biological periodontitis tests fall into four general categories and are designed to detect the presence of 1) substances associated with putative pathogens, 2) tissue breakdown products, 3) proinflammatory and immunological mediators, and 4) host-derived proteins, enzymes and substances.

Biochemical marker research of periodontal disease activity has focused its attention either on gingival crevicular fluid (GCF), peri-implant sucular fluid (PISF) or on saliva/mouthrinse samples. GCF is an inflammatory exudate that flows from inflamed human gingiva via the periodontal pocket to saliva. The degradative processes in diseased inflamed human gingival tissues are reflected in adjacent GCF and PISF, respectively. In clinical practice, GCF is easily collected by placing filter paper strips at the periodontal pocket orifice. Similarly, PISF is collected from the peri-implant orifice. Thus, GCF and PISF are attractive sources of potential markers for the progression of periodontitis. The advantage of GCF and PISF analysis is the site-specificity in regard to non-affected and affected sites. The disadvantage is in small sample volumes and technical difficulties in sample collection. On the other hand, in saliva/mouth-rinse samples the concentrations of the inflammatory mediators/enzymes are often diluted and do not reflect site specificity.

Tests for presence of putative periodontal pathogens

Much work has been done to determine which microorganism(s) are associated with progressing periodontitis (Armitage, G. C., Periodontal diagnostic aids, C.D.A. Journal 36, 35–41, 1993). In untreated patients with periodontitis, for example, the following bacteria (alone or in various combinations) have been suggested as putative pathogens: spirochetes (such as *Treponema denticola*), *Porphyromonas* (Bacteroides) *gingivalis, Bacteroides forsythus, Prevotella* (Bacteroides) *intermedio, Campylobacter rectus* (*Wolinella recta*), *Eikenella corrodens, Actinobacillus actinomycetemcomitans, Fusobacterium nucleatum, Capnocytophaga sputigena, Peptostreptococcus micros, Streptococcus mitis. Selenomonas* sp., *Eubacterium* sp. and *Haemophilus* sp. etc. These organisms have been identified in subgingival plaque samples by cultural analysis, microscopic examination, and by DNA probe analysis (Armitage, G. C., C.D.A. Journal 36, 35–41, 1993).

The BANA/BAPNA-test, based on hydrolysis of benzoyl-arginine-naphtylamide/benzoyl-arginine-p-nitroanilide, has identified the same putative pathogens (Armitage, C. G., C.D.A. Journal 36, 35–41, 1993). Since it is not known with certainty which of these organisms (if any) are responsible for the progression of periodontitis, their presence may not reflect actual periodontal disease activity.

Measurement of tissue breakdown products

One of the major features of periodontitis is the destruction of the extracellular matrix (i.e. collagen) of the periodontium. Type I and III collagens are the predominant collagen types present in periodontium.

Increased concentrations of hydroxyproline and glycosaminglycans have been shown in gingival crevicular fluid of periodontitis patients. Specific N- and C-terminal collagen telopeptides have been studied in periodontitis gingival crevicular fluid. These collagen type I and III propeptides in gingival crevicular fluid are suggested to reflect both gingival collagen synthesis and degradation (Talonpoika, J., Ann. Univ. Turku, Serie D 142, 1994). However, instead of reflecting the gingival collagen degradation they may reflect more efficient collagen synthesis/turnover in general, and have been valuable when monitoring periodontal healing after periodontal treatment rather than actual periodontal destruction associated with active periodontal disease progression (Talonpoika, J., et al., J. Clin. Periodontol, 21. 320–333; 1994).

An indicator of bone resorption is the measurement of collagen breakdown fragments, containing the pyridinoline intermolecular crosslinks (these are relatively unique to calcified tissues), which are released into biologic fluids (e.g., GCF, urine, serum) during extracellular destruction of bone (and cartilage). The measurement of these pyridinoline-containing collagen fragments in serum and urine is currently used as a diagnostic "marker" of active bone resorption during metabolic bone diseases such as hyperparathyroidism, post-menopausal osteoporosis, Paget's disease, and the arthritides (Greenwald R A, *Arth Rheumat* 39:1455–1465, 1996; Garnero P, Grimaux M, Sequin P, and Delmas P D, *J Bone Min Res* 9:255–264, 1994.) Giannobile et al. adapted the serum assay developed by Risteli et al. (1993), to monitor alveolar bone loss by measuring pyridinoline crosslinked carboxyterminal telopeptide fragments of type I collagen (ICTP) in GCF of periodontal pockets (Giannobile W V, Lynch S E, Denmark R G, Paquette D W, Fiorellini J P, and Williams R C, *J Clin Periodontol* 22:903–910, 1995; Giannobile W V, Palys M, Howell T H E, Haffajee A D, and Socransky S S, *J Dent Res* 75 (Spec. Issue):IADR abstract #1114 1996). Longitudinal studies on experimentally-induced periodontitis in dogs demonstrated that the detection of elevated levels of pyridinoline-containing fragments of type I collagen (this type of collagen makes up over 90% of the organic matrix of bone) in GCF preceded the detection of osseous metabolic activity and bone loss assessed by measuring bone-seeking radiopharmaceutical uptake and subtraction radiography, respectively (Giannobile W V, et al., J Clin Periodontal 22:903–910, 1995.). These pyridinoline-containing type I collagen fragments in GCF have also been reported to be positively correlated with clinical parameters of periodontal disease severity in humans, including radiologic assessment of alveolar bone loss, and were found to be decreased by conventional treatment such as scaling and root planing (Giannobile W V et al., J Dent Res 75 (Spec Issue):IADR abstract#1114, 1996, Talonpoika J T et al., J Clin Periodontol 21:320–326 1994). However, these assays do not provide a reliable, simple and rapid chair-side test. On the contrary, these assays are time-consuming and require expensive equipment. Moreover, such assays lack specificity since they may reflect the breakdown of collagen from inflamed tissue as well as from bone.

Measurement of proinflammatory and immunological mediators

Periodontal tissues and especially some distinct cells connected with gingivitis and periodontitis are known to produce a variety of proinflammatory and immunological mediators. Some of these have been suggested as biochemical/immunological markers in the assessment of periodontal disease activity (Page, R. C., J. Periodont. Res. 26, 533–546, 1991). Increased amounts of these proinflammatory mediators are detected in diseased gingival tissue and gingival crevicular fluid relative to periodontally healthy gingiva and gingival crevicular fluid (Page, R. C., J. Periodont. Res. 26, 533–546, 1991). Tumor necrosis factor-α, interleukin-1β and prostaglandin E2 have been subject of research (Page, R. C., J.

Periodont. Res. 26, 533–546, 1991). As these mediators reflect the activity of the inflammatory process, they show promise as markers. Moreover, it has been observed that these bone-modulating cytokines (IL-1β and TNF-α) were elevated in GCF at sites undergoing orthodontically-induced bone resorption, but not at inactive sites (Uematsu S, Mogi M, Deguchi T, *J Dent Res* 75:562–567, 1996). Yet none of them has proven to be specific enough to periodontal disease. Moreover, rapid tests for the detection of these bone modulating cytokines has not been developed.

In vitro these proinflammatory mediators are known to be capable of inducing de-novo MMP-expression by resident oral cells (gingival fibroblasts and keratinocytes) (Birkedal-Hansen, H. J. Periodontol. 64, 474–484, 1993). In vivo, increased amounts of the inflammatory mediators in periodontitis gingiva and gingival crevicular fluid are not associated with increased amounts of fibroblast-type MMPs (MMP-1 and MMP-2). These types of MMPs, in contrast to the PMN-type MMPs, are expressed and produced by resident gingival/oral fibroblasts and epithelial cells. Neutrophil-derived MMPs and elastase are found in periodontitis gingiva, gingival crevicular fluid and salivary/mouthrinse samples (Suomalainen, K., Thesis, Univ. Helsinki, 1993; Ingman, T., Thesis. Univ. Helsinki, Finland, 1994). Therefore, the relationships of the inflammation mediators (tumor necrosis factor-α, interleukin-1-β and prostaglandin E2 etc.) to MMP-dependent periodontal tissue destruction despite promising in vitro results (Birkedal-Hansen, H., J. Periodontal. 64, 474–484, 1993) is unclear (Sorsa, T., et al., Ann. N.Y. Acad. Sci. 732, 112–131, 1994).

Tests based on host-derived proteins enzymes and substances

The tissue destruction associated with the progression of periodontal disease/periodontitis lesions could be due to the independent and cooperative action of various host and bacterial derived proteolytic enzymes. During the development and progression of periodontitis lesions, various enzymes including matrix metalloproteinases (MMPs), elastase, cathepsin and trypsin-like proteinases etc. are released from triggered host cells. To some extent the proteinases may also be derived from oral bacteria (Uitto V-J, et al., Proc. Finn, Dent. Soc., 83, 119–130, 1987). Therefore, several proteinases, proteases and enzymes of this type have been suggested as biochemical markers for monitoring the progression and activity of periodontal disease (Armitage, C. G., C.D.A. Journal, 36, 35–41, 1993).

Test methods based on identification and measurement of enzymes/proteins and their activities have been developed. For example, aspartate aminotransferase (ASAT) has been associated with periodontal disease. This enzyme has been measured in gingival crevicular fluid, an inflammatory exudate of adjacent gingiva known to reflect the actual gingival cell tissue health (Page, R. C., J. Periodont, Res. 26, 230–242, 1991). ASAT is, however, released by almost all damaged cells in various periodontal tissues and is also present in blood in significant amounts. Therefore, a gingival crevicular fluid ASAT test is hampered by high nonspecific background.

False positives caused by enzymes released in conditions other than active periodontal disease are a major problem when using most of the other suggested enzymes (e.g. β-glucuronidase, lactate dehydrogenase, arylsulfatase, and some proteinases). Chair-side tests have been developed for gingival fluid elastase (Prognostick, Dentsply Corp., York, Pa.) and general proteinase activities (Periocheck®, Advanced Clinical Technologies Inc., Westword, Mass.). Both these tests lack specificity. The synthetic peptides and gelatin used as substrates are degraded by almost all human and bacterial proteinases. Therefore, high background activities, false positive, and false negative results have been found when enzyme activity is correlated with the clinical course of periodontal disease as compared with periodontally healthy controls.

A chair-side calorimetric protease assay system has been suggested for diagnosing periodontal diseases from saliva/mouthrinse, gingival crevicular fluid and dental plaque samples (Periocheck®, Advanced Clinical Technologies Inc., Westword, Mass.) has been developed.

The test known as the BANA/BAPNA-test, is based on hydrolysis of benzoyl-arginine-naphtylamide/benzoyl-arginine-p-nitroanilide. Hydrolysis results in red-orange color that indicates the presence of anaerobic oral bacteria such as *Porphyromonas gingivalis, Treponema denticola* and *Bacteroides forsythus* (Armitage, C. G., C.D.A. Journal, 36, 35–41, 1993). These organisms are thought to release trypsin-like proteases capable of hydrolyzing the synthetic BANA/BAPNA-peptide substrates. However, this test is not specific solely to bacterial proteinases. Many host cell derived proteinases (such as trypsins, trypsin-like proteinases, mast cell tryptases etc.) have similar specificities for BANA/BAPNA-peptides (Ingman, T., et al., Oral Microbiol, Immunol, 8, 298–305, 1993). Human cell-derived trypsin-like proteinases in periodontitis gingival crevicular fluid have been shown (Sorsa, T., et al., J. Dent. Res. 71, 732, 1992). Thus, a problem with this test is that it does not distinguish between host-cell derived and bacterial proteinases.

In summary, in the above-described assays, because of the involvement of various host and bacterial derived proteinases in the degradation of non-specific synthetic or natural substrates, such as gelatin, false negative and positive results often occur.

Matrix Metalloproteinases (MMPs) in periodontal diseases

Enzymatic degradation of periodontal connective tissue accounts for various alternations that are characteristic of diseased periodontal tissues. These include the net reduction of collagen(s), decreased strength and increased permeability of periodontal/gingival tissue, and alveolar bone loss.

Loss of collagen can result from changes in collagen metabolism. The rate of synthesis by fibroblasts may be decreased in inflamed tissue; the collagen synthesized may include defects in molecular structure of fiber formation. These changes would render collagen more susceptible to proteolytic degradation. It has been shown that polymeric collagen fibrils containing intermolecular crosslinks are considerably more resistant to proteolytic/collagenolytic degradation than are soluble collagen fibrils.

Collagenolytic enzymes (collagenases, gelatinases and stromelysins, members of the matrix metalloproteinase (MMP) family) are a host cell-derived proteinase group that has been thoroughly studied in the context of periodontal disease. In culture conditions, explants of inflamed gingiva secrete more collagenase than do explants from clinically healthy gingiva. A number of lines of in vivo evidence implicate host cell-derived matrix metalloproteinases (MMPs) in human periodontal tissue destruction (Birkedal-Hansen, H., J. Periodontal. 64, 474–484, 1993). Evidence includes elevated collagenase activity (MMP-1 and MMP-8) and gelatinases (MMP-2 and MMP-9) in extracts of inflamed gingival tissues, gingival crevicular fluid and salivary/mouthrinse-samples of periodontitis patients (Sorsa, T., et al., Ann. N.Y. Acad. Sci., 732, 112–131, 1994). The activities of these proteinases have been found to be positively correlated with the severity of periodontal inflammation and pocket depth at the periodontitis lesion sites donating these proteinases to gingival extracellular matrix and adjacent gingiva (Sorsa, T., et al., Ann. N.Y. Acad. Sci., 732: 112–131, 1994). However, no statistically significant correlation has been found of actual loss of bone density associated with periodontal diseases and these proteinases.

The relative amount of these proteinases recovered in active rather than latent form appears to increase with the greater severity of the periodontal disease (Suomalainen, K., Thesis, Univ. Helsinki, Finland, 1993). Further, the activities of these MMPs in periodontitis sites decrease after instrumentation therapy (scaling and root planing) (Ingman, T., Thesis, Univ. Helsinki, Finland, 1994). Further, increased collagenase activity has been found in gingival crevicular fluid during experimental gingivitis (Sodek, J., et al., Matrix 12 (Suppl. 1), 352–362, 1992). Finally, more collagenase can be extracted from inflamed human gingiva than from less inflamed gingiva (Sorsa, T., Thesis. Univ. Helsinki, Finland, 1989).

These results are thought to reflect changes in mammalian MMP activity because the proteinases recovered from diseased sites degrade triple helical collagen into the ¾- and ¼-fragments that are characteristic of mammalian collagenase cleavage (Sorsa, T., Thesis, Univ. Helsinki, Finland, 1989; Sodek, J., et al., Matrix 12 (Suppl. 1), 352–362, 1992). Recent studies on collagenases in gingivitis/periodontitis in gingiva, gingival crevicular fluid, and saliva/mouthrinse samples have utilized the difference in cleavage patterns of collagen by vertebrate and bacterial collagenase to identify the origin of the collagenases (Sorsa, T., et al., Ann. N.Y. Acad. Sci., 732; 112–131, 1994). For example, collagen type I was incubated with gingival extracts of inflamed human gingiva, gingival crevicular fluid (GCF) and peri-implant sucular fluid (PISF) samples; then, the reaction products were analyzed. The results consistently showed a cleavage pattern characterized by human rather than bacterial collagenase. Thus, collagenase of gingival tissue, GCF and PISF samples has been proven to originate mainly from human cells and not from bacteria (Sorsa, T., et al., Ann. N.Y. Acad. Sci., 732: 112–131, 1994). Recent studies have also shown that salivary and dental plaque collagenases from human supragingival and subgingival dental plaque samples are of human origin. It has been suggested that these collagenases have functional and immunological characteristics of MMP-8 in active form (Sorsa, T., et al., J. Clin. Periodontal., 22: 709–717, 1995). Thus, it appears that collagenase in periodontal disease is derived mainly from the host.

Further characterization of gingival tissue, gingival crevicular fluid, and salivary/mouthrinse collagenases/MMPs have revealed that the predominant source of the enzymes are polymorphonuclear neutrophilic leucocytes (PMN) present in periodontal inflammation. This is based on studies of the substrate specificity against type I–III collagens, response to procollagenase activators, and Western-blot and immunochemical analysis using specific anti-MMP antibodies (Sorsa, T., et al., Ann. N.Y. Acad. Sci. 732, 112–131, 1994). Tonetti, M. S., et al., have recently noticed that transcripts of neutrophil collagenase (MMP-8) can be found in inflamed human gingival tissue (Tonetti, M. S., et al., J. Periodont. Res. 28, 511–513, 1993).

If measured as total gingival crevicular fluid (GCF) and salivary collagenase or gelatinase activities, these proteinases have been found to be positively correlated with inflamed gingival tissue collagenase and gelatinase activities (Kinane, Curr. Op. Dent. 2, 25–32, 1992). Periodontal treatment results in decreased gingival crevicular fluid, salivary/mouthrinse PMN MMP-activities, close to those detected in healthy oral fluid samples (Sorsa. T. Thesis, Univ. Helsinki 1989; Suomalainen, K. Thesis, Univ. Helsinki, Finland, 1993; and Ingman, T. Thesis Univ. Helsinki, Finland, 1994).

Additionally, several studies have recently demonstrated that specially-formulated, low-dose regimens of doxycycline (LDD) can serve as matrix metalloproteinase inhibitors by suppressing the collagenase activity in the gingival crevicular fluid (GCF) and gingival tissues of patients with adult periodontitis (AP) (Golub, L M, et al., J Amer Dent Assoc 125:163–9 (1994), Golub, L M et al., J Periodontal Res 25:321–30 (1990)). In two subsequent placebo-controlled, double-blind clinical trials (one a multi-center study of 12 months duration), this regimen was also found to reduce pocket depth, improve periodontal attachment levels and inhibit alveolar bone loss in such patients (Crout, R J et al., J Periodontal 67:506–14 (1996), Caton, B J et al., J Dent Res 76 (Spec Issue):IADR abstract #1307 (1997)). Since LDD is an effective therapy for periodontal disease, the correlation between biochemical indicators, such as the MMPs, and the severity of periodontal disease can be assessed.

Several methods have been described to measure collagenolytic enzyme activity in saliva or gingival crevicular fluid. Activity can be measured spectrophotometrically by observing the increase in absorbance caused by collagen degradation (227 nm) (Lindy, S., et al., Eur. J. Biochem. 158, 1–4, 1986). Also, the degradation of a synthetic peptide as substrate connected to a color or fluorescence forming system can be followed spectrophotometrically or correspondingly, fluorometrically (Tschesche, H. et al., In Methods in Enzymatic Analysis, Bergmeyer, U. H. ed., Verlag Chemic, Weinhein, Germany pp. 239–248, 1985). With these methods, differentiation between individual collagenases is possible and can be achieved by specific inhibitors and activators (Sorsa., T., et al., Thesis Univ. Helsinki, Finland, 1989).

Matrix Metalloproteinase-8 (MMP-8) in periodontal and peri-implant diseases

MMP-8 (also known as collagenase-2 or neutrophil collagenase) is produced as procollagenase (proMMP-8) by human polymorphonuclear neutrophilic leucocytes (PMNs). Sorsa T., et al. have suggesed that MMP-8 is the key member of the collagenase/MMP-group. MMP-8 was said to be specifically involved in the progression of tissue destruction seen in periodontal disease. In fact, MMP-8 was suggested to be the primary MMP in the initiation of gingival/periodontal and alveolar bone tissue destruction in periodontal diseases. (Sorsa, T., et al., J. Periodont. Res. 23, 386–393, 1988; Sorsa, T., et al., Arch. Oral. Biol. 35, 193–6, 1990;

Golub, L. M., et al., J. Clin. Periodont., 22, 100–109, 1995; Sorsa, T., et al., Ann. N.Y. Acad. Sci. 732, 112–131, 1994; Ingman, T., et al., J. Periodontol 64, 82–88, 1993). Also periodontitis associated with HIV (+) Infections/AIDS diseases (Robinson, P. G., et al., J. Periodont. 65, 236–243, 1994; Holmstrup, P., et al., J. Clin. Periodontol. 21, 270–280, 1994) was found to be associated with increased activities and amounts of MMP-8. (Salo., T., et al., Ann. N.Y. Acad. Sci., 732, 476–478, 1994). Also inflammatory processes associated with peri-implantitis were suggested be associated with the increased activities and levels of MMP-8 in peri-implantitis gingival crevicular fluid (Ingman, T., et al., J. Clin. Periodontol. 21, 301–307, 1994; Teronen, O., et al., J. Dent. Res. 76: 1527–1537, 1997).

MMP-8 from the GCF, PISF and salivary/mouthrinse samples of periodontitis and peri-implantits patients have been found to be converted from inactive, latent proforms to catalytically active forms by periodontal and peri-implant inflammation (Sorsa, T., et al., J. Peridont. Res. 23, 386–393, 1988; Uitto, V., et al., J. Periodont. Res. 25, 135–142, 1990). The activation of gingival crevicular fluid and salivary pro-MMPs in periodontitis could result from independent and/or co-operative action of other human/PMN-proteinases (for example, cathepsin G, elastase), bacterial (*P. gingivalis* and *T. denticola*) proteinases and PMN-generated reactive oxygen species (such as hypochlorous acid. HOCl) (Sorsa, T., et al., N. Engl. Med. 321, 327–328, 1989; Sorsa, T., et al. Infection and Immunity 60, 4491–95, 1992; Sorsa, T., et al., Semin. Arth. Rheum. 22, 44–53, 1992).

A method which uses monoclonal antibodies which recognize the active mammalian MMP-8 has been disclosed (U.S. Pat. No. 5,736,341). The method is capable of differentiating between the active MMP-8 and its inactive proform. A chair-side test has been suggested for the detection of MMP-8 in the GCF, PISF or on saliva/mouthrinse samples by use of this method.

As will be shown below, however, the levels of MMP-8 in the GCF, PISF or saliva do not correlate well with the hard tissue destruction (bone loss) associated with periodontal diseases. MMP-8 is directly related instead to the soft tissue destruction (connective tissue destruction) that takes place during periodontal diseases.

As discussed above, a multitude of methods for assessing periodontal disease activities has been developed. However, none of these methods provide an adequate test to diagnose the bone destruction characteristic of periodontal diseases. The visual examination does not provide a diagnosis and an assessment of the progression of bone destruction. Clinical observations are not reliable enough because even deep pockets are not necessarily inflammatory active. Radiographic evaluations have to be combined with detailed clinical observations and visual examinations. The presence of pathogenic microorganisms do not fully reflect actual periodontic disease activity. Diagnoses based on breakdown products have not been satisfactory either because the presence of breakdown products may indicate rapid turnover or synthesis of collagen not necessarily degradation thereof. Proinflammatory mediators have been studied but no sufficiently rapid and specific test has been designed. Tests based on several host-derived enzymes have been developed, but most of them are not specific due to false positives caused by enzymes released by bacteria.

As mentioned above, although a rapid chair-side test which uses monoclonal antibodies has been suggested for MMP-8 (U.S. Pat. No. 5,736,341), the levels of MMP-8 in the GCF, PISF or saliva are not good indicators of the bone loss associated with periodontal disease. MMP-8 is directly related, instead, to the soft tissue destruction and inflammation which takes place during periodontitis.

A biochemical marker test that detects periodontal disease activity in a simple, practical, and reliable manner requires sensitivity and specificity. Sensitivity is the probability that the disease is present when the test results are positive. Specificity is the probability that the disease is absent when the test results are negative. In the progression of periodontitis, an optimal test would detect all progressing periodontitis sites without registering false negative results (optimal sensitivity) and all nonprogressing sites without registering false-positive results (optimal specificity).

In view of the above considerations, it is clear that existing methods for diagonosing the hard tissue destruction associated with periodontal disease are limited in a number of ways. For example, the existing art does not provide a rapid, chair-side diagnostic test and assessment for the loss of bone density associated with periodontitis, peri-implantitis and HIV(+)-infection/AIDS-disease related periodontal diseases. The lack of a diagnostic test revealing and monitoring the bone resorption (hard tissue destruction) associated with periodontal disease activity has been a serious problem, particularly in view of the severity of the corrective measures typically required to be taken to treat the bone destruction of periodontal disease. Thus, it is important to find biochemical markers which correlate with bone resorption.

Accordingly, it is an object of this invention to overcome the above limitations presently encountered in the art, by providing a method of monitoring the course and treatment of the bone loss associated with periodontal diseaes with a rapid and reliable chair-side assay.

SUMMARY OF THE INVENTION

It has now been discovered that these and other objectives can be achieved by the present invention which provides methods for monitoring the course and treatment of periodontal diseases, peri-implantitis or HIV(+)-infection/AIDS-disease related periodontal diseases. This method involves collecting a gingival crevicular fluid (GCF), peri-implant sucular fluid (PISF), saliva or mouthrinse sample; contacting the sample with at least one substrate which recognizes mammalian matrix metalloproteinase-13 in the sample; and detecting the presence of mammalian matrix metalloproteinase-13. An increased level of MMP-13 indicates periodontal disease, peri-implantitis or HIV(+)-infection/AIDS-disease related periodontal diseases.

The present invention also provides test kits for monitoring the course and treatment of periodontal diseases, peri-implantitis or HIV(+)-infection/AIDS-disease related periodontal diseases. This kit includes at least one detectable label and at least one substrate which specifically recognizes mammalian matrix metalloproteinase-13 (MMP-13) in gingival crevicular fluid, peri-implant sucular fluid, saliva or mouthrinse samples. An increased level of MMP-13 indicates periodontal disease or peri-implantitis or HIV(+)-infection/AIDS-disease related periodontal diseases.

BRIEF DESCRIPTIONS OF THE DRAWINGS

FIG. 1 is a graph illustrating ICTP and Osteocalcin levels in the GCF of adult periodontitis subjects during a two month period.

FIG. 2 is a graph illustrating ICTP and Osteocalcin levels in the GCF of adult periodontitis subjects during a two month regimen of low-dose doxycycline.

FIG. 3 is a graph illustrating ICTP and Collagenase activity in the GCF of adult periodontitis subjects during a two month regimen of low-dose doxycycline.

FIG. 5 is a graph illustrating the relation between the gingival index and the bone resorption score of dental implants.

DETAILED DESCRIPTION OF THE PREFERRED EMBODIMENTS

Figure 4A:
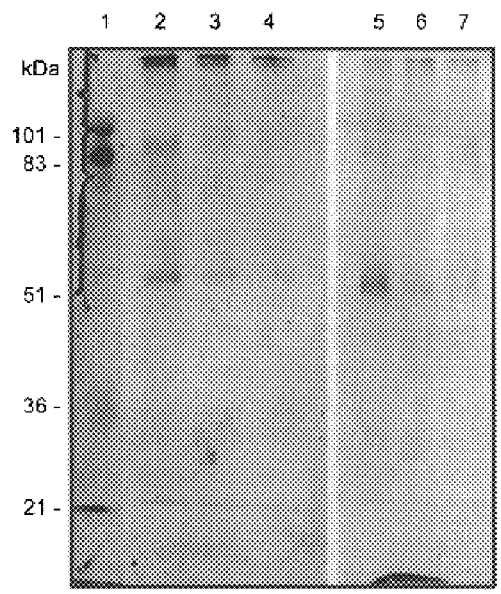
FIG. 4 is a Western blot illustrating the effect of a two month regimen of low dose doxycycline on MMP-13 levels in the GCF of two representative adult periodontitis subjects.

The destruction of bone is the most pernicious pathological event associated with periodontal and peri-implant diseases. Therefore, there is a great need for a marker which detects the destruction of bone. An advantage of measuring MMP-13 in the GCF, PISF and saliva of periodontitis and peri-implantitis patients is that MMP-13 is directly related with the bone resorption associated with periodontal and peri-implant diseases. MMP-8, on the other hand, relates to the soft tissue inflammatory response. Although MMP-8 is the dominant collagenase in the GCF and saliva of periodontal pockets ($\approx$95% of the total GCF), the levels of MMP-8 present do not correlate well with the hard tissue destruction (bone loss) associated with periodontal diseases. It is surprising that MMP-13, which appears only as a trace amount in the GCF, PISF and saliva of periodontal patients is the key collagenase in a diagnostic test for periodontal diseases.

The advantage of measuring MMP-13 in the GCF of periodontal patients compared with measuring the inflammatory cell collagenase, MMP-8, has been demonstrated in two studies performed by the inventors.

The inventors demonstrated that MMP-13 in PISF reflects bone destruction during failing of dental implants (peri-implantitis). In the study PISF samples were collected with filter paper strips from subjects with varying degrees of radiologically detected vertical bone resorption. An assessment was made in each subject of gingival inflammation (GI), elastase activity and MMP-13 immunoreactivities of their PISF samples. There was a weak relation between the severity of peri-implant GI and the irreversible bone resorption. Elastase activity in PISF samples did not correlate with the bone resorption. The levels of the MMP-13 immunoreactivities, however, correlated clearly with the increasing score of bone resorption. MMP-13 was found to reflect and to a great extent be responsible for the irreversible peri-implant bone destruction. (See Example 1.)

The inventors demonstrated that MMP-13 in GCF reflects the inhibition of the progression of adult periodontitis due to treatment with low-dose doxycyline (LDD); a therapy which reduces the severity of periodontitis by inhibiting collagenase in periodontal tissues and pockets. In the study GCF was collected from subjects with periodontitis. Some of the subjects were treated with low dose doxycycline. As the LDD therapy continued there was a reduction in levels of collagen degradation fragments. In this study MMP-13 was detected in human GCF for the first time. A decrease of GCF MMP-13 correlated with the reduction of collagen degradation fragments. MMP-8 did not demonstrate such a correlation. (See Example 2.)

The invention relates to biochemical means and methods, especially immunological means and methods for monitoring the course and treatment of periodontal diseases. In particular, this invention relates to methods and test kits for diagnosing and assessing the progression of the loss of bone density associated with periodontal diseases. Additionally, this invention relates to methods and test kits for screening for the risk of periodontal diseases. The methods and kits of the invention provide a reliable, sensitive and selective diagnosis and assessment of the progression of the bone destruction associated with periodontal disease activity, peri-implantits or HIV(+)-infection/AIDS-disease related periodontal diseases. The preferred methods and test kits of this invention are constructed to be easy and rapid chair-side tests. The methods and means of the invention apply to mammals, particularly humans.

These and other advantages of the present invention will be appreciated from the detailed description and examples that are set forth herein. The detailed description and examples enhance the understanding of the invention, but are not intended to limit the scope of the invention.

The methods and kits of the invention are based on the preparation and use of substrates which recognize mammalian matrix metalloproteinases-13 (MMP-13). The inventors have found that the collagenase-3/MMP-13 ("bone-type collagenase"), when used in assays, is an excellent diagnostic test for the hard tissue destruction, such as bone resorption, of periodontal diseases.

MMP-13 is produced as about 65 kD procollagenase by bone cells (osteoblasts and osteoclasts). MMP-13 is thought to play an important role in the destruction of calcified connective tissues during arthritic and other diseases. Particularly, MMP-13 is thought to play a important role in bone destruction. Furthermore, MMP-13 is associated with bone resorption in vitro which is independent of the inflammatory response. Since MMP-13 is produced by bone and cartilage, MMP-13 was initially reported to be associated strictly with bone and cartilage cells. Recently MMP-13 has been found to be present in soft tissue. (Uitto, V J et al., 77: J of Dent Res 1998) The inventors have surprisingly found MMP-13 to be present in the GCF and saliva of periodontal pockets.

General principles of immunoassays and the generation and use of antibodies as laboratory and clinical tools are set forth, for example, in Antibodies, A Laboratory Manual (Harlow, E. and Lane, D. eds. Cold Spring Harbor Laboratory. Cold Spring Harbor, N.Y. 1988).

DEFINITIONS

Unless defined otherwise, all technical and scientific terms used herein have the same meanings as is commonly understood by one skilled in the art to which this invention belongs. In the description, as follows, a number of terms used to immunology and dentistry are extensively used. In order to provide a clear and consistent understanding of the specification and claims, including the scope to be given such terms, the following definitions are provided.

"Antigen" refers to any composition, organism, or material that is capable of eliciting an antibody response specific for that composition, organism, or material.

"Chair-side test" refers to a test or procedure which may be performed while the patient is in the dental, medical and/or veterinary office, as in the dental, medical or veterinary operatory, by dental, medical or veterinary office personnel.

"Periodontal disease" refers to a disease of the supporting structures of the teeth or the periodontium, which typically includes both soft tissue inflammation and loss of alveolar bone support. It also includes peri-implantitis and HIV(+)-infection/AIDS-disease related periodontal diseases.

"Peri-implantitis" refers to the state of soft and bony tissue inflammation effected by stable implants which have been surgically implanted into the alveolar bony ridge. "Peri-implantitis" is included in the term "periodontal disease."

"Gingivitis" refers to a condition wherein the gingivae, or attached mucosal soft tissues of the mouth are in a state of inflammation.

"Monitoring the course and treatment" of periodontal diseases includes diagnosing for periodontal diseases, assessing the progress of the periodontal diseases and screening for the risk of periodontal diseases.

"Substrate", as used in the claims, includes any molecule that binds specifically to MMP-13, typically a protein, more typically an antibody. Antibodies include monclonal antibodies, polyclonal antibodies and fragments of monclonal and polyclonal antibodies. Proteins which bind specifically, but are not antibodies, can be found by screening any library of chemicals with MMP-13. The substrates of this invention include any molecule which binds specifically to either or both the active and inactive site of MMP-13.

"Metalloproteinase" refers to the family of collagenases that include human bone-type collagenase-3 (MMP-13), human polymorphonuclear leukocyte (PMN) collagenase-2 (MMP-8) and human fibroblast collagenase-1 (MMP-1). Metalloproteinases are synthesized by mammalian cells. Recombinant human/mammalian MMPs can be synthesized by certain bacterial cells. They are initially synthesized in an inactive or "proenzyme" form and become enzymatically active if they are cleaved to create or expose the enzyme's active site. The generation of the active site may be effected by chemical or enzymatic cleavage of the proenzyme either in vivo or in vitro. In vivo, enzymes are capable of generating the active site and may be bacterial or endogenous, i.e. mammalian origin. The proenzyme may also be referred to as the "proform" or "latent enzyme."

"Isoform" refers to the different forms of the same protein. For example, active collagenases of metalloproteinase MMP-13 are generated by the cleavage of the proenzyme to form an active enzyme with an exposed active site, as noted above. Different reactions, including different enzymatic reactions, are capable of creating an active enzyme. These varied reactions cleave the proenzyme differently, generating different molecular species called isoforms. In the present invention the antibodies which recognize the proenzyme preferably recognize the part of the enzyme which is common to the active and inactive form of the enzyme.

"Site-specific sampling" refers to a method or procedure wherein the material to be sampled is solely in a distal periodontal and peri-implantitis lesions to effect the testing of intracrevicular fluid only from the distal periodontal and peri-implant lesion pocket.

"Direct label" refers to a label that allows detection of an antibody or an antigen in an assay wherein the detectable label is directly attached to antibody or antigen taking part in the principal immunoreaction.

"Indirect Label" refers to any label that allows detection of an antibody or antigen in an assay wherein the detectable label is not directly attached to the antigen or antibody taking part in the principal immunoreaction but is added to the reaction mixture to indicate that the immunoreaction has occurred.

"Solid carrier" refers to a solid medium or solid phase to which an antibody is attached. For example, when proteins such an antibodies are attached to latex beads, colloidal metal, polyvinylchloride (PVC) and polystryene *Staphylococcus aureus* Protein A or nitrocellulose membranes, those proteins are attached to solid carriers.

"Liquid carrier" refers to a liquid medium or liquid phase that is capable of effecting the movement of a composition, such as an antibody or antibody-conjugate complex, wherein the composition diffuses with the liquid.

"Immunoassay" refers to a method or procedure capable of detecting and/or measuring a substance wherein the active and specific reagents include at least one substrate capable of specifically binding said substance. Basic types of immunoassays include antigen capture assay, antibody capture assay and antibody sandwich assays which are defined below.

"Two Antibody Sandwich Assay" refers to an immunoassay capable of detecting or quantitating the amount of substrate, such as an antibody or antigen in a sample. The assay requires the use of two different antibodies capable of binding two different, non-overlapping (noncompetitive) epitopes on an antigen.

"Lateral Flow Technique" refers to an immunoassay using immunochromatographic principles. It is typical for the test that the sample or test solution which is in liquid form moves along a test strip in contrast to the "Flow-Through Technique" in which the test solution is allowed to flow through a membrane in a test device.

"Flow Through Technique" is an immunoassay often based on the sandwich technique. The antigen containing sample or test solution is applied as a spot and is allowed to diffuse through a membrane in device. "RIA" or "radioimmunoassay" refers to immunoassays wherein the detectable label is a radiolabel in the form of a radioisotope attached to an antigen.

"IRMA" or "immunoradiometric assay" refers to an immunoassay wherein the detectable label is a radiolabel in the form of a radioisotope attached to an antibody.

"Enzyme immunoassay" refers to any immunoassay which includes the use of enzymes as active reagents. For example, the enzyme may be attached to a primary or secondary antibody. The enzyme may react with a chromogenic substrate.

"Fluoroimmunoassays" refers to any immunoassay which includes the use of fluorescent substances as detectable labels.

"Luminescence immunoassays" refers to any immunoassay which includes the use of luminescent substances as detectable labels.

"Immunoagglutination assays" refers to any immunoassay which uses agglutination of particles by multivalent antigens as the means of detecting an immunospecific reaction. For example, when purified antibodies are attached to red blood cells or colored beads and multivalent antigens reactive with said antibodies are added to the immunospecific antibody/antigen reaction leads to aggregation or agglutination of said particles.

"Turbidimetric immunoassay" refers to any immunoassay which uses the measurement of turbidity of particles by multivalent antigens as the means of detecting an immunospecific reaction. For example, aggregation of antibody-conjugated particles by multivalent antigens and optionally further enforced by using microparticles may create a measurable turbidity to an otherwise clear solution.

"Nephelometric immunoassay" refers to a variant of the Turbidimetric immunoassay".

The invention relates to test kits providing means to practice the methods of the invention using substrates to diagnose periodontal diseases. The test kits and methods according to the present invention may contain several substrates that recognize different forms of mammalian, preferably a human, MMP-13 and at least one label. This label may be attached to the substrate. The test kits and methods may also provide means for differentiating between active MMP-13 and inactive proMMP-13. It is to be understood that the mammalian MMP-13 and proMMP-13 encompass MMP-13 and pro-MMP-13 from any given mammal. However, it should be recognized that human is the most preferable species. Of course, domestic and veterinary animals are also included.

The preferred substrates of this invention are antibodies. The antibodies can be polyclonal or monoclonal, but are preferably monoclonal. Also any fragments of monoclonal or polyclonal antibodies having the requisite characteristic can be used, for example, single chain antibodies. Single chain antibody fragments, each having one $V_H$ and one $V_L$ domain covalently linked by a first peptide linker, can be covalently linked by at least a second peptide linker to form a multivalent single chain antibody. Multivalent single chain antibodies are within the scope of this invention. Multivalent single chain antibodies include bivalent dimers, also known as diabodies. Multivalent single chain antibodies also include trivalent trimers, also known as triabodies.

Different types of test kits can be constructed to suit the immunological method which has been selected. Carrier materials and accessories are included in the test kits depending upon the method desired. The method is preferably chosen among immunochromatographic methods, immunometric methods, radioimmunoassays, radioimmunometric assays, enzyme immunoassays, fluoroimmunoassays, luminescence immunoassays, immunoagglutination methods, hemagglutination methods, inhibition of agglutination methods and turbidimetric immunoassays. The detectable labels and optional carriers are selected according to the appropriate method.

The most preferred test kits of the present invention for chair-side use are constructed according to immunochromatographic methods based on the lateral flow principle or an immunometric method based on the flow-through principle.

The test kits can contain an optional second substrate, which recognizes mammalian MMP-13. The second substrate need not differentiate between the pro MMP-13 and the active MMP-13. This second substrate is also preferably labeled with at least one detectable label selected from a group consisting of direct or indirect labels. This second substrate is preferably an antibody. The second antibody can be monoclonal or polyclonal or a fragment thereof.

The method for diagnosing periodontal disease activity is essentially performed as an immunological assay including the following steps. Gingival crevicular fluid sample is collected with a sampling device. Simple solid devices can be used for collecting site-specific samples. In an optional embodiment of the invention the sampling device is also used as the test device. The sample is then contacted with at least one monoclonal antibody, which is already attached to the sampling or test device or can be added to the combined sampling and test device. Alternatively, the sampling device can be added to the test device which contains the monoclonal antibody. In a preferred method, periodonal disease activity is detected by a site-specific method in which the sample is collected with a solid absorbing sampling device which can act as a test device.

Binding of the substrate with MMP-13 is then detected. See below.

According to one embodiment, the risk for periodontal diseases and peri-implantitis activity can be prescreened by testing for an increased level of MMP-13 in a salivary sample or a mouthrinse sample. The prescreening activity can be performed as an immunological assay using the following steps. A salivary or mouthrinse sample containing GIF or PISF is collected and the sample is then contacted with at least one antibody which recognizes MMP-13. An increased level of MMP-13 is detected by an immunological method.

The invention also encompasses a set of test kits for chair-side diagnosis. In each test kit at least one substrate recognizes mammalian MMP-13. The set may be provided in a packaged combination containing one or more prescreening test kits and one or more mouthrinse vials and one or more site-specific test kits, which in addition to the substrate contains one or more sampling devices. These prescreening and site-specific test kits can be provided in combinations of variable numbers which allow the prescreening of, for example, all children in a school class and site-specific confirmation tests of those who have an increased level of MMP-13.

The methods and materials used to develop the test kits and the methods of the present invention are discussed in more detail below.

Collagenolytic enzyme activities in salivary/mouthrinse, GIF and PISF samples can be assessed by various known methods. The inventors have been able to estimate the amount of latent proMMP-13 and active MMP-13 in salivary/mouthrinse, GIF and PISF samples from adult periodontitis patients, as well as from periodontally healthy individuals, by ELISA, SDS-PAGE and Western blot.

Genetically different collagenases (MMP-1, MMP-2, MMP-8 and MMP-13) have also been identified by Western blotting; that is, after SDS-PAGE of the enzyme preparations bands have been transferred onto nitrocellulose and characterized by fluoroimmunologic staining with labelled polyclonal antibodies to MMP-13 and other enzymes to be studied With methods like this, a more specific result in regard to actual cellular source and degree of activation of collagenase/MMPs is obtained but they are far too laborious and time consuming to be used in routine laboratory work. Moreover, it is impossible that a rapid chair-side test would be based on any kind of electrophoresis.

The level of MMP-13 in case of direct site-specific sampling of GCF, PISF and saliva which indicates a risk for periodontal disease activity or peri-implantitis has been determined by a specific immunoblot technique: for GCF>10 $\mu$g/ml; for PISF>10 $\mu$g/ml; and for saliva>10–20 $\mu$g/ml. (See Table A.)

TABLE A

MMP-13 in GCF, PISF and Saliva from Untreated Adult Periodontitis Patients (n = 7) & Periodontally Healthy Individuals (n = 7) (determined by specific immunoblot technique)

| Patient Group | Oral Fluid | MMP-13 Concentration ($\mu$g/ml) | |
|---|---|---|---|
| | | Active | Total |
| Healthy Controls | GCF/PISF | 0 | 3–7 |
| Healthy Controls | saliva | 0 | 4–10 |

TABLE A-continued

MMP-13 in GCF, PISF and Saliva from Untreated
Adult Periodontitis Patients
(n = 7) & Periodontally Healthy Individuals (n = 7)
(determined by specific immunoblot technique)

| Patient Group | Oral Fluid | MMP-13 Concentration ($\mu$g/ml) | |
|---|---|---|---|
| | | Active | Total |
| Adult Periodontitis | GCF/PISF | 20–45 | 25–55 |
| Adult Periodontitis | saliva | 25–50 | 35–60 |

In another embodiment of this invention, the methods and test kits include, in addition to a substrate which recognizes MMP-13, a substrate which recognizes MMP-8. The molar ratio of MMP-13 to MMP-8 in the PISF and GCF are evaluated. In one study the inventors have found that the risk indicator-ratio of MMP-13:MMP-8 of oral fluids to be approximately greater than 1/30 to 1/25. (See Table B.)

TABLE B

Molar Ratio of MMP-13:MMP-8 in GCF and PISF from Untreated
Adult Periodontitis Patients, Healing/Treated Patients and
Periodontally Healthy Individuals

| Patient Group | Oral Fluid | MMP-13:MMP-8 |
|---|---|---|
| Adult Periodontitis | GCF | 1:20 |
| Healing/Treated | GCF | 1:20–1:25 |
| Healthy | GCF | 1:40–1:25 |
| Bone Resorption Grade = 1 | PISF | 1:20 |
| Bone Resorption Grade = 2 | PISF | 1:20 |
| Bone Resorption Grade = 3 | PISF | 1:40–1:50 |

Developing Antibodies

Monoclonal antibodies of the present invention may be developed by methods known in the art, such as the original technique of Kohler and Milstein (Nature 256, 495, 1975). The inventors have used the specific application thereof published by Stenman U., et al. (J. Immunol. Meth. 46, 337, 1981).

In the present invention, immunization scheme uses different molecular isoforms of MMP-13 as immunogens to allow selection for antibodies reactive with common epitopes. The crucial point, however, is the system to test hybridomas and clones. Hybridomas are screened with one isoform that occurs widely in patients. The clones developed are further tested against various types of active MMP-13 before the final choice of a broadly reactive antibody.

In immunization, a crude preparation of MMP-13 is initially used, but in the last booster the presence of different molecular forms is ensured by using a mixture of highly purified, active and nonactive MMP-13 preparations.

Proenzyme proMMP-13 may be partially purified from cultured cells by methods known in the art, such as the technique of Lindy, O, et al. (Arth Rheum 40: 1391–1399, 1997). For the last booster, the antigen is further purified and used as a mixture of proenzyme isoforms activated by, for example, 1) autoactivation. 2) treating with an oxidant, and 3) enzymatic degradation with a human and bacterial proteinase (for human cathepsin G: Saari, H., et al. Biochem. Biophys. Res. Commun. 171, 979–987, 1990); *T. denticola* chymotrypsin-like protease; (Sorsa, T., et al., Infection and Immunity 60, 4491–95, 1992). Alternatively, individual mice can be boosted with one isoform.

Autoactivation of the MMP-13 preparation may be performed by methods known in the art, such as the technique of Lindy, O, et al. (Arth. Rheum. 40:1391–1399, 1997). For oxidant activation, NaOCl is employed as the oxidating agent and activation is performed essentially as described (Saari, H., et al., Biochem. Biophys. Res. Commun. 171, 979–987, 1990). The method of Sorsa, T., et al. (Sorsa, T., et al J Biol Chem 272: 21067–21074, 1997; Infection and Immunity 60: 4491–95, 1992) is used for activation with proteinases obtained from human cells and *T. denticola*.

Monoclonal antibodies having essentially the same properties obtainable by essentially the method described above, or by a technique essentially the same as above but also using other screening criteria, or obtainable by other conventional methods for preparing monoclonal antibodies, as well as polyclonal antibodies, are within the scope of this invention. For example, the phage display method described in the patent publications WO 90/14443 and WO 92/18619, which are hereby incorporated by reference, can also be used.

The following discloses one embodiment of the invention.
Immunization, fusion, cloning and transplantation of clones.

BALB/c mice are immunized and boosted intraperitoneally with 300–500 $\mu$l of a solution containing 50–100 $\mu$g/ml of crude active MMP-13. This is done by injection in Freund's incomplete adjuvant at 2–4 week intervals. If the mice have an antibody titer after the first boost, they are boosted intravenously with 50–100 $\mu$g of the antigen mixture described above in saline. The spleen is removed 3–4 days after the last booster. 1–2×10$^8$ spleen cells are fused in polyethylene glycol (PEG. Boehringer Mannheim Cat. No. 1243268) with 2.5–5.0×10$^7$ P3×63-Ag8.653 myeloma cells (Syngeneic) in exponential growth phase. After fusion, cells are plated into U-bottomed microplates in Dulbecco's modified Eagle's medium (DME) with 15% horse serum or RPMT-1640 with 7.5% horse serum at a density of 2×10$^6$ cells/ml. Each well contains 0.1 ml of culture medium. After 1 day, 0.1 ml of selective HAT medium (2% mixture of hypoxanthine, aminopterin and thymidine in DMEM, Gibco 50x HAT. Cat. No. 043-01060H) is added to the cultures. After this, half of the medium is removed every other day and replaced with fresh HAT medium.

After 2 weeks of culture the cells are transferred to HT culture medium (2% HAT without aminopterin, Gibco 50x HT. Cat. No. 043-01065H), which is changed three times a week for two weeks. After 2 weeks the culture medium is replaced with DME+15% horse serum or RPMT-1640 and 7.5% horse serum. Vigorously growing antibody-producing cultures are screened and characterized as described. The cultures of selected hybridomas are then cloned by limiting dilution in flat-bottomed microtiter plates on human fibroblast feeders. Antibody-producing clones are recloned in 96 well plates. Subclones are expanded in test tubes and later in Falcon tissue culture flasks.

For transplantation of the hybrid clones, antibody-producing cells (1×10$^6$/animal) are injected intraperitoneally into BALB/c recipients primed with pristane (2,6,10,14-tetramethylpentadecane. Aldrich). Ascites develops within 3–4 weeks. The ascitic fluid is withdrawn and the antibody in the fluid tested.

Screening and titration

The supernatants from the cultures are screened for antibody production preferably at weekly intervals from hybridization or cloning. Titrations of the antibodies are preferably performed weekly. Antibody titration is also carried out on antisera from immunized mice and in ascites fluid.

To detect antibody production against MMP-13, a radioimmunoassay (RIA) is used. Radioiodinated activated, highly purified MMP-13 is used.

When titrating, the titer is defined as the dilution binding 50% of the maximum amount of label specifically bound by a large excess of antibody. Polyclonal antiMMP-13 recognizing both inactive proenzyme and active MMP-13 is used as control antibody.

Methods of testing and characterization

The positive hybridoma cultures are further tested for their sensitivity to detect active MMP-13, i.e. their reactivity with active MMP-13 and for their cross-reaction with the proenzyme. An RIA method is used. The label is the same preparation of radioiodinated trypsin-2 activated MMP-13 mentioned above in the screening assay. 100 $\mu$l of label, 50 $\mu$l of standard or the cross-reactant to be tested and 50 $\mu$l of antibody solution (all in phosphate-EDTA-NaCl buffer containing 0.33% BSA, pH 7.4) are incubated overnight. Separation of bound radioactivity is performed similarly to the screening method. Each antibody is diluted to bind about 50% of its maximal binding capacity. Standards are prepared from trypsin-2 activated MMP-13 in concentrations ranging 10–1000 $\mu$g/l.

The hybridomas with best sensitivity and with no cross-reaction with other MMPs are selected to be cloned. The specificities of the new monoclones are further characterized. For use in the diagnostic test, clones are selected that react as equally as possible with all of the isoforms. The epitope common to all the isoforms may be the enzyme active site. The clones are also tested for their cross-reaction to enzymes structurally and immunologically related to MMP-13 which may be present in gingival crevicular fluid samples (e.g., MMP-8, PMN-gelatinase (MMP-9) fibroblast type collagenase (MMP-1) and stromelysin-1 (MMP-3).) Preferably, clones producing cross-reactions >0.1% (defined as percentage of the cross-reactant concentration of standard concentration that will cause a 50% displacement of the label) are not selected. The immunoglobulin isotype produced by the selected clones is determined by a kit method (Mouse Typer. BioRad, California). The antibodies are purified by affinity chromatography with Protein A (Pharmacia, Sweden) and their isoelectric points are recorded by isoelectric focusing (Phast System. Pharmacia, Sweden) using standard techniques.

Diagnostic test methods for determining periodontal disease activity.

The monoclonal antibodies specific to human and/or mammalian MMP-13 developed according to the above procedure are used for designing a variety of test methods useful in the assessment of periodontal disease activity. Quantitative and qualitative methods are described below.

A standard method for immunologically detecting the presence of an antigen is visually observing agglutination of antibody-coated particles caused by antigen binding. The particles include latex particles. Part of the latex particles are coated with monoclonal antibodies specific to one epitope of MMP-13 and part are coated with antibodies specific to another epitope. When MMP-13 is present the two kinds of particles are bound in a network via antigen bridging and thus agglutination occurs. Red blood cells can be used as particles if a so-called hemagglutination test is provided. Inversely, the principle of inhibition of agglutination can be used.

A more recent method involves the use two antibodies in a flow-through immunometric technique (U.S. Pat. No. 4,366,241). The test is best performed in a device wherein a pad of absorbing material is covered by a membrane of, for example, nitrocellulose or nylon. On the membrane is an area on which antibodies of one kind (for instance, those recognizing the active site of MMP-13) are attached. Liquid sample is pipetted on the membrane and any active MMP-13 present in the sample will be bound to the antibodies. The rest of the sample will flow through the membrane. Then a labeled reagent is added. This label can be a conjugate of the second antibody (monoclonal or polyclonal antiMMP-13 recognizing an epitope other than the first antibody) and an enzyme like horseradish peroxidase. If there is any MMP-13 bound on the membrane the conjugate will bind to it and can be visualized by washing off excess conjugate and adding a precipitating substrate to the labeled enzyme. The precipitated substrate can produce a visible color. The substrate can also be one producing an invisible signal, for example, a fluorescence or chemiluminescence signal. Intensity of colour, fluorescence or chemiluminescence can be recorded by appropriate instruments and in these cases, if concentration calibration is used, the test result can be quantitated. The labeled reagent can also be a suspension of colored (or otherwise signal producing) particles (made of, for example, latex) that are coated with the second antibody. Here, the pore size of the membrane is so adjusted that those particles that are not immunochemically bound on the membrane will flow through the pores. After a washing step, the bound particles can be detected directly if visual or indirectly by signal measurement.

The periodontal disease activity test as described herein can be based on the immunochromatographic principle. This technique, often referred to as the lateral flow technique, has been described in detail in EP 291 194 which is incorporated herein by reference. U.S. Pat. No. 5,712,170 includes a test device that essentially consists of a membrane and an absorbing pad in a dipstick constructed with a chamber-like gap. In the immunometric version that employs two different antibodies, the first antibody is coated on particles that act as a label detectable by eye (color visible) or by suitable instruments (fluorescent or chemiluminescent signal producing). The particles can be made, for example, of latex, colloidal metal (gold selene) or a dispersing dye. These label particles are attached in a test device so that when the absorbing part of the device is brought into contact with the liquid sample and the sample is absorbed, the particles will migrate with the liquid flow and simultaneously, label antibody will bind the antigen (for example, active MMP-13) if present in the sample. The liquid will be further absorbed into the membrane in the device. On the membrane, a second antibody (monoclonal or polyclonal antiMMP-13 recognizing an epitope other than the first antibody) has been attached in a zone-like area. When the liquid flow carrying the label migrates through this zone, those label particles that have bound antigen will be bound to the zone. Thus, the zone will be detectable if there was antigen present in the sample.

This immunoassay technique can also be based on the use of one antibody only. This can be done by using antigen coated label particles in competition with antigen possibly present in the sample. The monoclonal antibody specific to MMP-13 is attached in a zone on the membrane. Sample antigen will occupy the antibody binding sites in the zone and thus no detectable zone will appear. In another version, labeled particles coated with an antigen analogue are loosely bound to the antibody attached in the absorbing area. Sample antigen will displace the analogue in antibody binding and label particles are able to migrate to a zone containing a capture reagent.

Immunochromatography can also be made quantitative by measuring the signal produced by a label that is bound to the membrane when known standards or unknown samples are run. Visual semiquantitation is possible if several antibody zones with increasing antibody amount in the zone are used in the test device.

The above mentioned immunoassay techniques are useful for the development of a rapid chair-side test with a short performance time (often only a few minutes). The more recent techniques (lateral flow and flow-through) will provide tests that can be performed and interpreted very reliably by personnel untrained to laboratory work. They also lack some major disadvantages connected with agglutination methods, such as, for instance, false positives with samples containing rheumatoid factor and difficult interpretation of especially turbid samples.

However, other immunological methodologies can be adapted in a test for assessing periodontal disease activity. These methods are usually performed in a laboratory because of the need for specific, possibly automated, instrumentation and/or trained personnel. The following techniques are also suitable if a quantitative test result is required. Turbidimetric and nephelometric methods can be used. They usually employ polyclonal antibodies, but the reagents can also consist of a mixture of latex particles of suitable size coated with two different antibodies. Classical immunochemical methodologies with radioisotopic labels can be applied (radioimnunoassay involving one antibody in a competitive assay design and immunoradiometry involving an antibody pair). Instead of isotopic labels, a variety of other labeling compounds are useful in related immunoassay methodologies. Enzymes like horseradish peroxidase or alkaline phosphatase can be conjugated to antibodies in order to act as labels in enzyme immunoassays or immunoenzymometric assays which labels are detected with the help of calorimetric, fluorometric or chemiluminometric substrates. Also, fluorescent compounds can be directly conjugated to antibodies and be used in quantitative fluoroimmunoassays or fluoroimmunometric assays where several sophisticated detecting methods have been developed (e.g. delayed fluorescence, fluorescence polarization). Together with the fluorescence methods, methods using luminescence producing labels (luminescence immunoassays or immunoluminometric assays) are the most sensitive immunochemical technologies available today.

Site-specific and screening tests for determining periodontal disease activity.

All the test methods described above can in principle be used in both site-specific and screening tests. However, visual agglutination, flow-through and immunochromatographic methods are best suited to a rapid chair-side test. These techniques are optional for both site-specific and screening tests.

In a screening test the aim is to find out if increased total MMP-13 is present in the patient's GIF, PISF, saliva or mouthrinse samples.

Saliva is easily collected after letting the patient first rinse his mouth thoroughly and then chewing paraffin. Other stimulants of saliva excretion can also be used. If it is necessary to store the specimen before analysis, a specific saliva collection device like Omni-SAL® (Saliva Diagnostic Systems, Wash.) can be used. Alternatively, the test can be performed in a mouthrinse specimen which is collected by allowing patients to chew paraffin for 30 sec-1 min and subsequently spit the oral fluid contents; thereafter, the patients rinse their empty mouths with 3 ml of tap water which is then collected for testing.

For a site specific dipstick test, the dentist can collect a sample of GCF, and/or PISF by placing a filter paper strip at the periodontal pocket and/or peri-implant orifice. The strip is allowed to absorb liquid, for a standardized time. Then, the strip is transferred to a test tube with an adequate buffer solution where sample proteins are extracted. In case an immunochromatographic dipstick format is used, the dipstick is directly dipped into the tube for the test. Besides the filter strips other absorbing materials like porous plastics or ceramics as well as organic or inorganic silica compounds are also applicable, e.g. attached to a holder for convenient transfer. Liquid can be collected in a capillary tube of glass or plastic. Finally, a dipstick-type device can be so designed that it includes an absorbing end that is placed in the periodontal pocket and the sample is absorbed directly into test device.

A site-specific dipstick test for ruling out the possibility of periodontal disease and peri-implantitis in the individual site or directing the clinician to further studies can be quantified. The threshold value (cut-off concentration) for the test is chosen so as to give optimal sensitivity and specificity. In the case a periodontal disease activity test, total MMP-13 concentrations above about 10 ng/ml can be interpreted as positive in site specific samples. The corresponding values in salivary/mouthrinse samples are much more variable. Thus, in saliva/mouthrinse, values of above 10–20 ng/ml of total MMP-13 may suggest an increased risk of progressing periodontitis. A concentration of active MMP-13 above 15–20 ng/ml in a salivary sample indicates active disease in some sites which should then be individually tested.

EXAMPLE 1

Figure 6:
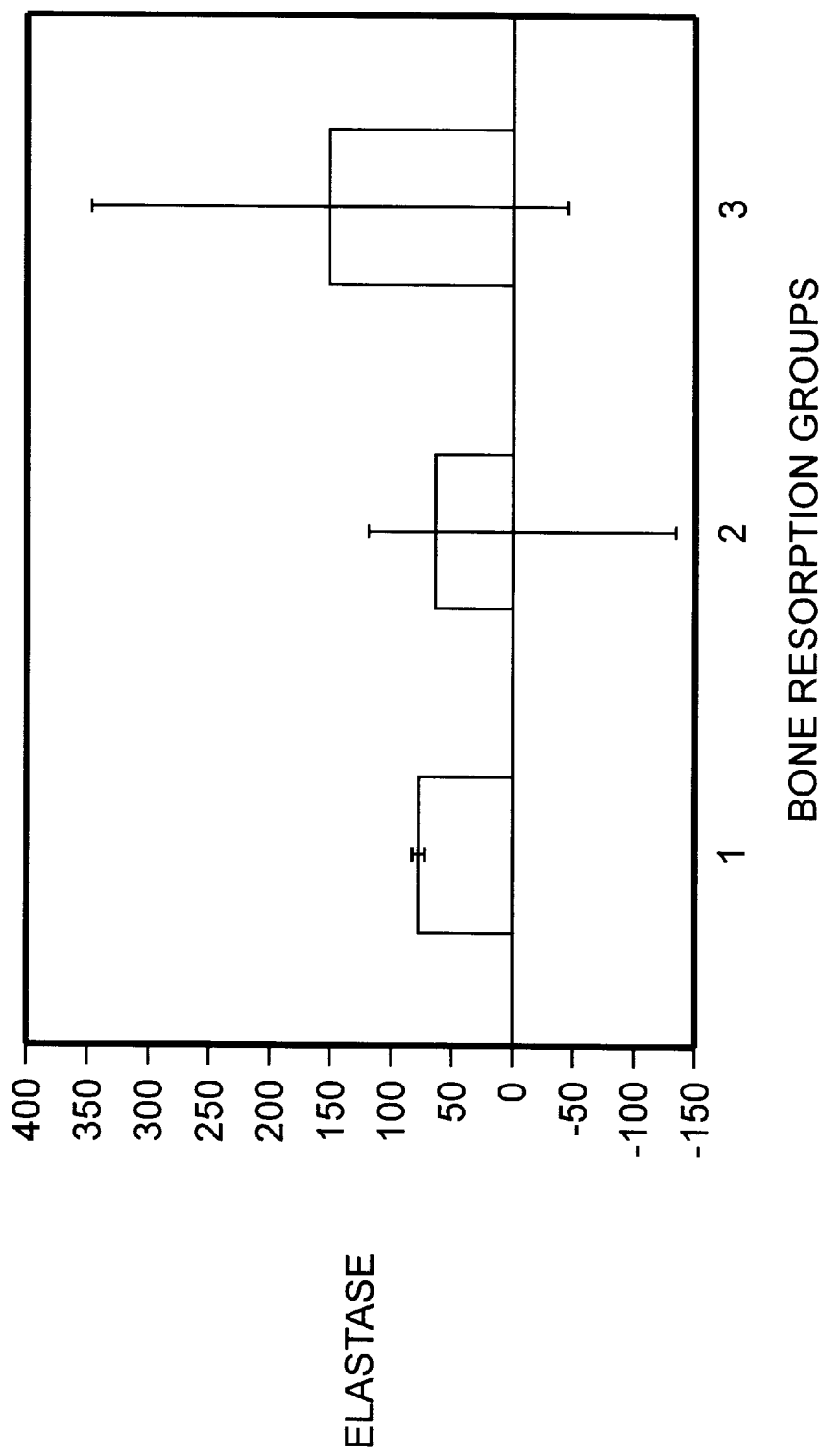
FIG. 6 is a graph illustrating the relation between the neutrophil elastase activity in PISF and the bone resorption score of dental implants.
Figure 7:
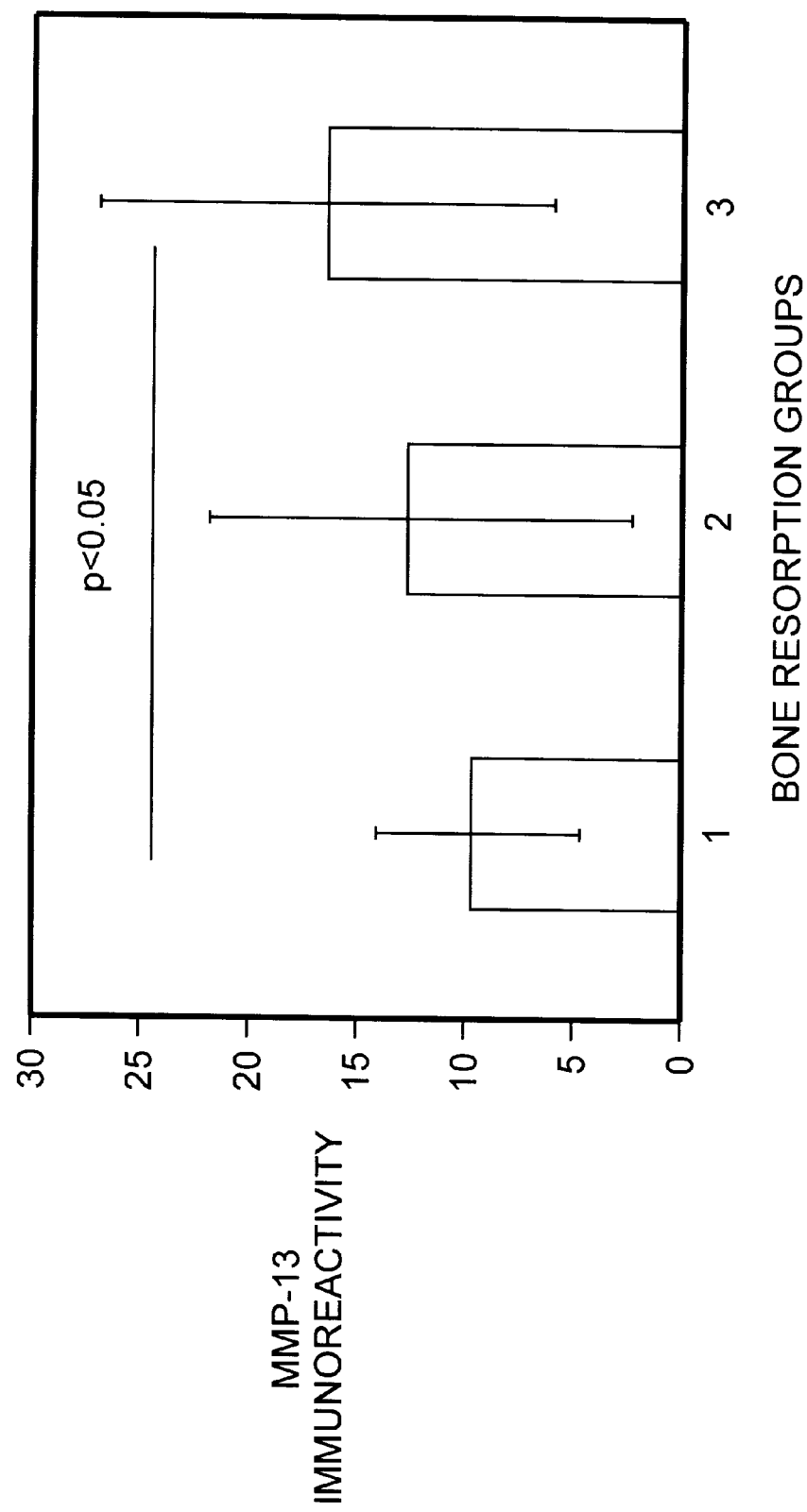
FIG. 7 is a graph illustrating the relation between the levels of the MMP-13 immunoreactivities in PISF and the bone resorption score of dental implants.

Peri-implant sulcular fluid (PISF) samples were collected with filter paper strips according to Teronen et al. J Dent Res 76: 1529–1537, 1997 from peri-implant margins of dental implants surrounded or affected with varying degrees of radiologically detected vertical bone resorption. Bone resorption grade 1 indicates less than 1 mm vertical bone resorption. Bone resorption grade 2 indicates vertical bone resorption between 1–2 mm. Bone resorption grade 3 indicates vertical bone resorption of more than 3 mm. In each bone resorption group n=10. In determining the radiologically detected bone loss (Jeffcoat, M K; Chung, W I; Reddy, M S; Radiographic Diagnosis in Periodontics. Periodontol 2000 7: 54–68, 1995) the junction area of distance and fixture of inserted dental implant was used as a reference (Branemark, 1985). Gingival index (GI) of peri-implant soft tissues was determined according to the principle of Loe H. (Gingival index (GI), the plaque index and the retention index system. J Periodontol 38 (Suppl): 610–616, 1967.) Thus the soft peri-implant mucosal tissue, peri-implant radiographs and the collected PISF samples were analyzed for GI, radiologically detectable bone loss, elastase activities (Iman et al. J Periodontol 65: 702–709, 1994) and MMP-13 immunoreactivities using a specific antibody with quantitative immnunoblot analysis (Golub et al., Inflamm Res. 36:310–316). The results showed that the GI of the peri-implant mucosa increased in relation to the radiologically detected bone resorption score of the studied dental implants. (See FIG. 5.) However, this finding was not statistically significant. Thus, there is a rather weak relation between the severity of the peri-implant mucosal inflammation and irreversible bone resorption of the dental implants. Clinical indices of peri-implant mucisitis are not sensitive enough to express the underlying irreversible bone resorption of dental implant affected by peri-implantitis. Neutrophil elastase activity (a biochemical marker of periodontal inflammation) in PISF did not correlate at all with bone resorption scores. (See FIG. 6.) There was less elastase activity in the group with a bone resorption score of 2 as compared with the group with a bone resorption score of 1, and slightly increased elastase activities were detected in the group with the bone resorption score of 3 as compared with the groups with bone resorption scores of 1 and 2. However, none of these observed differences were statistically significant (Student's t test). This indicates that solely neutrophil-derived biochemical markers in PISF do not reflect clearly enough the irreversible bond resorption associated with clinical loosening of dental implants affected by on-going peri-implantitis. The levels of the MMP-13 immunoreactivites correlated clearly and statistically significantly (Student's t test) with the increasing score of bone resorption in the studied dental implants. (See FIG. 7.) This suggests that a MMP-family-member, i.e. MMP-13/"bone-type collagenase" evidently produced by adjacent bone cells reflects and to the great extent is responsible for the irreversible peri-implant bone destruction leading to loosening and finally to the loss of dental implants. (See FIGS. 5, 6 and 7.)

EXAMPLE 2

Eighteen human subjects with varying severity of adult periodontitis (AP), assessed by clinical criteria (see below), including 8 males and 10 females ages 32–72 years, were enrolled in this open-label longitudinal study. At the 1st (or screening) appointment, before baseline, informed consent was obtained (the protocol and consent forms were reviewed and approved by the committee on research involving human subjects at SUNY at Stony Brook), a medical and dental history were taken, an oral examination performed, and each subject was given a 30-minute-timed scaling and prophylaxis using both ultrasonic scalers and hand instruments. The exclusion criteria applied to the subjects were the same as those described by us recently (Golub, L M, et al., Inflam Res 36: 310–316, 1997).

At the three subsequent appointments, Baseline (4 weeks after scaling and prophylaxis), 1-month and 2-months later, 8–12 preselected pocket sites in the right and left maxilla were monitored as follows: Precut sterile filter paper strips (Periopaper®, Proflow Inc., Amityville, N.Y.) were inserted for 10 seconds into each isolated and air-dried pocket until slight resistance was felt, the volume of GCF collected was immediately measured with the Periotron 6000® (Proflow Inc.) and the values recorded. The samples were immediately placed into microfuge tubes (Sarstedt, Numbrecht, Germany) on ice and transferred to $-80°$ C. for storage until analyzed for ICTP, osteocalcin, or collagenase activity (see below). Immediately after the GCF samples were collected for each subject, the following clinical measurements of disease severity were recorded for each pocket site: gingival index or GI, plaque index or PII, probing depth or PD, and attachment level or AL using the cementoenamel junction as the anatomical reference point. These measurements were carried out with a manual probe. In three groups of subjects, group I (n=6 subjects; mean age=55.2 years), group II (n=5 subjects; mean age=55.8 years), and group III (n=7 subjects; mean age=52.9 years), each of the 8–12 pocket sites selected per subject exhibited mild-moderately severe AP based on a GI score of 1–3, PD of 4–9 mm, and examination of clinical radiographs for alveolar bone loss. At the end of the baseline and 1-month appointment, each subject in groups II and III was given a 1-month supply of LDD (20 mg per capsule, to be taken twice daily) while those in group I were given no medication throughout the entire 2-month protocol. At the 1- and 2-month appointments, unused capsules were counted to assess compliance.

Measurement of GCF analytes (a) Pyridinoline-containing crosslinked carboxyterminal telopeptide breakdown products of type I collagen (ICTP).

This procedure was carried out as described previously (Golub et al., Inflam Res 36:300–316, 1997). The frozen GCF samples were thawed at room temperature, followed by elution of proteins by multiple (5×) centrifugation at 3,000 RPM for 5 min with 20 $\mu$L phosphate buffered saline (pH 7.4) containing 15 nM aprotinin, 1 mM PMSF, and 0.1% human serum albumin. ICTP was analyzed in the GCF extract by radioimmunoassay (RIA) as described by Risteli et al. (Clin. Chem 39:635–40,1993). This extraction procedure showed >90% recovery of ICTP from the filter paper strips, the assay has a sensitivity to detect ICTP at a concentration as low as 340 pg/mL (Incstar Corp., St. Paul, Minn.), and the data was expressed either as pg ICTP/pocket (10 second collection) or as ng ICTP/mL GCF. ICTP levels were measured in selected GCF samples from groups I, II and III (Note: ICTP and osteocalcin (see below) were measured in different pocket sites but in the same subjects in groups I and II, while collagenase was measured only in samples from group III subjects; see RESULTS section).

(b) Osteocalcin.

This technique was similar to that described by Kunimatsu et al. (J Periodontal 64:865–869 (1993). After thawing, each GCF sample was extracted in 70 $\mu$L PBS (pH 7.4) containing the proteinase inhibitors, 1 mM PMSF and 5 mM soybean trypsin inhibitor, for 15 min at 4° C. The extracts were then centrifuged at 10,000× g for 5 min at 4° C. and osteocalcin was measured by immunoradiometric assay, which detects both the intact bone matrix protein and its large N-terminal mid-fragment (Immutopics, Inc., San Clemente, Calif.), as follows: 10 $\mu$L of GCF extract or of standard human osteocalcin (the latter at concentrations ranging from 0.06–60 ng/mL) were incubated with 200 $\mu$L of $^{125}$I-labeled antibody to osteocalcin. The mixture was vortexed, then incubated with osteocalcin-antibody-coated beads at 22° C. overnight (18 hr) on a low-speed shaker water bath. The beads were then washed 3 times with 2 mL of 0.01 M PBS containing 0.05% $NaN_3$ and the radioactivity measured in a gamma counter (Cobra II Auto-Gamma, Packard Co., Meriden, Conn.) for 1 min. The osteocalcin level in each GCF sample was calculated from a standard curve and expressed either as pg/pocket (10 sec. collection) or ng/mL of GCF.

(c) Collagenase.

Collagenase activity.

The details for measuring GCF collagenase activity are described by Golub, L. H. et al. (Inflam Res 36:310–16, 1997). In brief, each filter strip containing GCF was extracted in 400 $\mu$L of 50 mM Tris-HCl buffer (pH 7.6) containing 0.2 M NaCl, 5 mM $CaCl_2$, 0.02% $NaN_3$ and 0.05% Brij 35; the samples were then centrifuged and sterilized through a 0.2$\mu$ microfilterfuge tube. A 70 $\mu$L aliquot of GCF extract was then incubated with 10 $\mu$L [$^3$H-methyl] collagen at 22° C. for 48 hr, in the presence or absence of aminophenylmercuric acetate (APMA) added in a final concentration of 1.0 mM to activate procollagenase. The reaction was stopped by adding 10× sample buffer and by boiling for 5 min. The intact a collagen components and the ¾ (or $\alpha^A$) collagen degradation fragments were detected by a combination of SDS-PAGE and fluorography. The conversion of the a components to the $\alpha^A$ collagenase digestion products was calculated after scanning the fluorograms with a laser densitometer (Golub, L M et al. Inflam. Res. 36:310–6, 1997).

Western blot analysis of MMP-8 and MMP-13.

GCF extracts (100 $\mu$L) from the Group III AP subjects were lyophilized with a Speed-Vac (Savant Instruments, Inc., Holbrook, N.Y.) and stored frozen at $-80°$ C. Each sample was then thawed and analyzed for both MMP-8 (collagenase-2) and MMP-13 (collagenase-3) levels (MMP-1 was measured in a separate group of AP subjects; see below) by Western blot analysis using a modification of techniques described by us Sorsa T, et al. (Ann NY Acad Sci 732: 112–131, 1994). Note: the human recombinant MMP-13 was produced in E. coli and purified to apparent homogeneity as described by Lindy. Antibodies to this protein were raised in rabbits, the IgG fraction was purified by DEAE-ion exchange chromatography, and immunoblot analysis showed no cross-reactivity with other MMPs such as collagenase-1, collagenase-2, gelatinases and stromelysins (Lindy et al. Arth. Rheum, 1997).

In brief, the lyophilized GCF extracts (containing approximately 2 μg protein) were treated with Laemmli's buffer (pH 7.0) containing 5 mM dithiothreitol and heated for 5 min at 100° C. High and low range pre-stained SDS-PAGE standard proteins were used as molecular weight markers. The samples were electrophoresed on 7.5% SDS-polyacrylamide gels then electrophoretically transferred to nitrocellulose membranes. Non-specific binding was blocked by incubation with phosphate buffered saline containing 5% non-fat dry milk (90 min, 37° C.). The membranes were then incubated with rabbit polyclonal antibodies specific for MMP-8 and MMP-13 diluted 1:500 (or with non-immune control serum diluted 1:100) for 1–6 hrs at 20° C. After repeated washings, the membranes were incubated with biotinylated anti-mouse immunoglobulins (1 hr, 20° C.), further incubated with anti-mouse antibody-alkaline phosphatase conjugate, an the color developed by standard technique. The Western blots were then scanned using an imaging densitometer (Bio-Rad Model G5-700, Richmond, Calif.), using the Molecular Analyst® Program (Image analysis system version 1.4) to determine the relative amounts of MMP-8 and MMP-13. The ratio, MMP-13/MMP-8, was calculated for the samples collected at time=0 (before LDD therapy), and at 1- and 2-months of LDD therapy.

Statistical analysis.

Statistical significance between the values for the different time periods was determined using one way analysis of variance (ANOVA) except for some of the data in Table 2, which were analyzed using paired student t-test. These analyses were carried out using SigmaStat statistical software (Jandel Scientific Software, San Rafael, Calif.).

Clinical Parameters of Periodontal Disease

During this short-term longitudinal study, periodontal disease parameters at selected sites were clinically assessed at baseline (time=0), 1 month and 2 months (Table 1). The control subjects (group I), exhibited no significant changes in any of these parameters over the 2-month study when compared to baseline (it should be recalled that all subjects in this study, Groups I–III, received a 30-minute scaling and prophylaxis 1 month before the time-0 appointment). However, both Groups II and III, in which all 12 subjects received daily regimens of LDD, showed statistically significant improvement in periodontal attachment levels ($p<0.05$). Of interest, the percent improvement in attaclunent levels after 2-months of treatment with LDD for Group II (which exhibited more severe AP based on greater PD and AL at time=0) and Group III subjects (which exhibited milder AP at time=0 based on these clinical parameters) was 27% and 18%, respectively, which was essentially twice the effect seen for both groups after 1 month of LDD treatment (Table 1). These results indicated that the more severe the disease, and the longer the duration of therapy, the greater the efficacy of LDD on periodontal attachment loss. The only other statistically significant change in clinical parameters of disease in this short-term longitudinal study was a reduction in GCF flow at the 1 and 2-month time periods ($p<0.05$) for both LDD-treated groups. During the 2-month regimen of LDD therapy, other improvements in parameters of periodontal disease seemed to occur, such as a 14–16% reduction in pocket depth and a 21–25% decrease in gingival index, but these effects were not statistically significant.

GCF Analytes (i) Pyridinoline crosslinked carboxyterminal telopeptide fragments of type I collagen (ICTP)

At the baseline appointment before LDD therapy, no significant differences for GCF ICTP levels (pg/site; 10 sec. collection) were detected between all three groups of subjects (FIGS. 1, 2, & 3). Only the control subjects (Group I) showed no significant changes in ICTP values over the 2-month experimental period (FIG. 1). In the two treatment groups, the LDD therapy markedly reduced GCF ICTP. These effects for both treatment groups (Groups II and III) were statistically significant ($p<0.05$) at both the 1 and 2-month time periods (FIGS. 2 and 3). In the subjects with more severe AP (Group II), GCF ICTP was reduced, compared to baseline values, by 66–68% at both time periods, and the subjects with less severe AP (Group III) showed only slightly less improvement (61–63% reduction) in this biochemical marker of tissue breakdown. A similar pattern of change was seen when ICTP was expressed as a concentration value (ng/ml of GCF). However, although these treatment effects, when the ICTP data was expressed as a concentration, were also statistically significant ($p<0.05$) for both groups (II and III) of AP subjects, the magnitude of the changes with time were less dramatic than expressing the data as pg/pocket site. This occurred because the volume of GCF collected per 10 sec (reflecting severity of gingival inflammation) was reduced as a result of the LDD therapy (Table I) although the amount of analyte in the GCF was reduced even more. Consistent with this observation, when GCF ICTP and the various clinical parameters of periodontal disease severity were correlated, the correlation coefficients were found to be more strongly positive when the GCF data was expressed on an "amount per site" rather than on a "concentration" basis, and only the former values were statistically significant.

(ii) Osteocalcin

GCF levels of osteocalcin are shown in FIGS. 1 and 2. When the osteocalcin data was expressed as amount (pg) per site (FIGS. 1 & 2) or as a concentration (ng/mL of GCF; data not shown), no significant differences could be seen between the control and LDD groups at the baseline appointment. When GCF osteocalcin levels were assessed temporally (expressed either as amount per site or as a concentration) in either Group I (controls) or Group II (LDD-treated) subjects, again no significant changes were observed. These observations demonstrated that osteocalcin was not significantly modulated by LDD therapy in these AP subjects. Accordingly, a third group of subjects (who, like Group II, were treated with LDD for 2 months) was added to this study and the GCF samples from these AP patients were analyzed for ICTP (to confirm the results observed in Group II subjects) and collagenase (see below), but not for osteocalcin.

(iii) Collagenase Assays

Collagenase activity was assessed in the GCF of 7 AP subjects (Group III) either in the presence or absence of APMA, which was added to the incubation mixture to activate Pro (or latent)-collagenase (note: only the data obtained in the presence of APMA is shown in FIG. 3).

Significant reductions in GCF collagenase activity were observed at both the 1 - and 2-month time points during LDD administration. However, the 26–32% reduction in collagenase (in the absence of APMA in vitro; data not shown) and the 34–42% reduction (when APMA was added to the incubation; FIG. 3) were less dramatic than the reductions in ICTP seen in the GCF produced by the two month LDD therapy (FIG. 3), but the effects measured in the presence or absence of APMA were both still statistically significant (p<0.05).

Figure 4B:
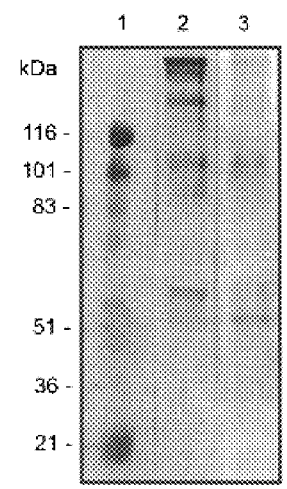

The GCF samples from these same 7 AP subjects were also examined for MMP-8 and MMP-13 levels during the 2-month protocol. Representative Western blots using polyclonal antibodies specific to MMP-13 are shown in FIG. 4, Panel A (MMP-8 data not shown). A prominent band with a molecular weight of about 60 kDa is seen in lanes 2 and 5 using GCF collected from 2 representative AP subjects (the data for the other 5 subjects not shown) before LDD treatment. Lanes 3 & 6 and 4 & 7 show reductions in MMP-13 protein levels in the GCF of these same two subjects one and two months after initiating LDD therapy, respectively. Densitometric scanning of the Western blots (Table 2) for all 7 AP subjects indicated that MMP-13 levels were reduced by 63% and 80% at the 1-month and 2-month time periods of LDD therapy, respectively (p<0.05 for both). It should be noted that several previous studies by our and other groups have demonstrated that MMP-1 is either not, or only minimally, detected in the GCF of AP patients (Ingman T, et al., J Clin Periodontol 23:1127–1132 (1996). Moreover, GCF samples from an additional 5 AP subjects were analyzed in the current study, using specific antiserum and immunoblot technique, and MMP-1 was again not detected.

The proportion of MMP-13 (collagenase-3) relative to MMP-8 (collagenase-2) in the GCF of these 7 AP subjects was estimated at about 3.5%. Since the level of both of these collagenases was reduced by about 60% after 1 month of LDD therapy, the ratio of these two MMPs remained unaltered at this time period (Table 2). However, after a 2-month regimen of LDD, the MMP-13/MMP-8 ratio in the GCF was found to be reduced by 60% (p<0.01) reflecting a preferential reduction in the level of bone-type (MMP-13), rather than leukocyte-type (MMP-8), collagenase (Table 2) as the therapy was prolonged beyond the 1-month time period.

Analysis of the Western blot data in the current study indicated that the GCF from these AP patients exhibited predominantly MMP-8, consistent with previous reports and that this collagenase was reduced about 60% during the 2 month protocol. However, this study also identified, for the first time, MMP-13 (collagenase-3) in the GCF of periodontal pockets. MMP-13, expressed by bone and cartilage (and other) cells, is homologous to rodent fibroblast-type collagenase and is thought to be a mediator of bone resorption and cartilage destruction during diseases such as rheumatoid- and osteo-arthritis. Although the data in the current study indicates that MMP-13 comprised only 3–4% of the total collagenase in the GCF (the rest was primarily MMP-8; little or no MMP-1 or collagenase-1 has been or was (current study) detected in the GCF of adult periodontitis patients), the AP subjects in this study demonstrated a substantial reduction (60–80%) in this "bone-type" collagenase during LDD therapy. In fact, the response of MMP-13 to LDD exceeded the reduction in MMP-8 in these periodontal pockets as the host-modulating therapy was prolonged. Thus, at the end of the 2-month regimen of LDD, MMP-13 only comprised about 1.4% of the collagenase detected in the GCF, rather than the 3.5% present before this therapy.

Additional recent experiments indicate that MMP-13, like MMP-8, is much more sensitive to doxycycline inhibition in vitro that MMP-1, supporting the hypothesis that TC therapy suppresses pathologically-excessive collagenase activity (e.g., MMP-8 and MMP-13) associated with inflammatory and bone/cartilage-destructive diseases. However, the Western blot analysis indicated that most of the MMP-13 in the GCF was recovered as a single band of 55–60 kDa. This suggests that most of this enzyme in the current study was present either as the pro-form or the partially-active intermediate form; the fully-active MMP-13, characterized by a molecular weight of 48 kDa (see FIG. 4, Panel B, lane 3), was not detected (note that the purified MMP-13 standard, FIG. 4, Panel B, exhibited several bands in addition to the 60 and 48 kDa forms of this proteinase; these have been described previously as dimeric aggregates/dimers (higher molecular weight forms) and autocatalytic degradation products (lower molecular weight forms) generated during storage). These higher molecular weight proteins detected in the Western Blot (see FIG. 4, Panel A), e.g., about 90 kDa and another near the origin, represent active MMP-13 complexed to the endogenous proteinase inhibitors TIMPs and $\alpha_2$-macroglobulin, respectively.

TABLE 1

Clinical Parameters of Disease in Control and LDD-treated Adult Periodontitis Subjects

| Group | Timepoint (months) | GCF ($\mu$l) | GI score | PD (mm) | AL (mm) | PlI score |
|---|---|---|---|---|---|---|
| Control | 0 | 0.50 ± 0.06 | 1.4 ± 0.18 | 4.9 ± 0.43 | 6.6 ± 0.60 | 1.06 ± 0.1 |
| Group I | 1 | 0.53 ± 0.07 | 1.5 ± 0.16 | 4.7 ± 0.35 | 7.3 ± 0.50 | 1.39 ± 0.15 |
| (n = 6) | 2 | 0.53 ± 0.07 | 1.5 ± 0.18 | 5.1 ± 0.46 | 6.6 ± 0.60 | 1.35 ± 0.13 |
| LDD | 0 | 0.51 ± 0.07 | 1.61 ± 0.14 | 5.7 ± 0.41 | 7.5 ± 0.46 | 1.34 ± 0.19 |
| Group II | 1 | 0.31 ± 0.05* | 1.12 ± 0.15 | 5.0 ± 0.37 | 6.5 ± 0.43* | 0.86 ± 0.16 |
| (n = 5) | 2 | 0.35 ± 0.06* | 1.18 ± 0.14 | 4.8 ± 0.38 | 5.5 ± 0.57* | 0.89 ± 0.17 |
| LDD | 0 | 0.47 ± 0.03 | 1.41 ± 0.10 | 4.9 ± 0.20 | 6.1 ± 0.40 | 1.27 ± 0.09 |
| Group III | 1 | 0.30 ± 0.03* | 1.09 ± 0.09 | 4.3 ± 0.20 | 5.5 ± 0.50 | 1.14 ± 0.08 |
| (n = 7) | 2 | 0.26 ± 0.03 | 1.05 ± 0.07 | 4.2 ± 0.20 | 5.0 ± 0.40* | 1.09 ± 0.63 |

Values are mean ± S.E.M. for each site.
*p < 0.05 compared to baseline.

TABLE 2

The Effect of a 2-month Regimen of LDD on the Relative Amounts of MMP-8 and MMP-13 in GCF of AP (Group III) Subjects[1]

| Duration of LDD Therapy | MMP-8 (collagenase-2)* | MMP-13 (collagenase-3)* | MMP-13 as % of Total Collagenase in GCF |
|---|---|---|---|
| Baseline | 926 ± 52 | 35 ± 11 | 3.5 ± 0.9 |
| 1 month | 365 ± 117[#] | 13 ± 7[#] | 3.6 ± 0.8 |
| 2 months | 305 ± 153[#] | 7 ± 4[#] | 1.4 ± 0.5[¶] |

[1]Each value represent the mean ± S.E.M. for 7 subjects.
*Arbitrary units based on densitometric scanning of Western blots.
=Calculated assuming no detectable MMP-1 (collagenase-1) in GCF of AP subjects (see ref. no. 31,33).
[#]$p < 0.05$ vs. baseline determined by ANOVA.
[¶]$p < 0.01$ vs. time 1 month or baseline determined by paired t-test.

Legends to Figures

FIG. 1. ICTP and osteocalcin levels in GCF (both markers expressed as pg per pocket site) of adult periodontitis (AP) subjects during a 2-month longitudinal open-label study. These controls (Group I) received no medication, however all subjects in Groups I, II and III received a 30 minute-timed scaling and prophylaxis 4 weeks prior to the baseline appointment. Each value represents the mean±standard error of the mean (S.E.M.) of 24 pocket sites for ICTP and 19 sites for osteocalcin measurements in 6 control subjects.

FIG. 2. ICTP and osteocalcin levels (pg/site) in GCF of AP subjects (Group II) before and during a 2-month regimen of low-dose doxycycline (LDD). Each value represents the mean±S.E.M. of 20 pocket sites for ICTP and 22 sites for osteocalcin measurements in 5 LDD-treated subjects.

FIG. 3. ICTP levels (pg/site) and collagenase activity (% [$^3$H-methyl] collagen α components degraded to $\alpha^A$ fragments during incubation with 1.0 mM APMA at 22° C.) in GCF of AP subjects (Group III) before and during a 2-month regimen of LDD. Each value represents the mean±S.E.M. of 28 pocket sites for ICTP and collagenase assays in 7 LDD-treated subjects.

FIG. 4. Effect of a 2-month regimen of LDD on MMP-13 (or collagenase-3) levels in GCF of two representative AP subjects assessed by Western blot analysis. Panel A: Lane 1, prestained molecular weight protein standards; Lanes 2 & 5, MMP-13 levels in GCF of these 2 subjects at the pre-treatment or baseline appointment; Lanes 3 & 6, MMP-13 levels in the GCF of these subjects after 1 month of LDD therapy; Lanes 4 & 7, GCF MMP-13 levels in these subjects after 2 months LDD. Panel B: Lane 1, pre-stained molecular weight protein standards; Lanes 2 & 3, purified MMP-13 (400 ng) standard in the absence or presence of APMA (1.2 mM final concentration), respectively.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method for monitoring the course and treatment of periodontal disease or peri-implantitis wherein the detection comprises the steps of:
    (a) collecting a gingival crevicular fluid, peri-implant sucular fluid, saliva or mouthrinse sample;
    (b) contacting said sample with at least one molecule which recognizes mammalian matrix metalloproteinase-13 in said sample; and
    (c) detecting the presence of said mammalian matrix metalloproteinase-13, wherein an increased level of MMP-13 indicates periodontal disease or peri-implantitis.

2. The method of claim 1, wherein at least one of the one molecules recognizing MMP-13 is an antibody.

3. The method of claim 2, wherein the antibody is a monoclonal antibody.

4. The method of claim 2, wherein the antibody is a polyclonal antibody.

5. The method of claim 2, wherein the antibody is a fragment of a monclonal or polyclonal antibody.

6. The method of claim 1, wherein the molecule that recognizes MMP-13 is labeled with a label selected from the group consisting of direct and indirect labels.

7. The method of claim 1, wherein said mammalian matrix metalloproteinase-13 is a human matrix metalloproteinase-13.

8. The method of claim 1, which additionally comprises a molecule which recognizes mammalian matrix metalloproteinase-8 (MMP-8).

* * * * *